(12) United States Patent
Majer et al.

(10) Patent No.: US 8,703,700 B2
(45) Date of Patent: Apr. 22, 2014

(54) BIMACROCYCLIC HCV NS3 PROTEASE INHIBITORS

(75) Inventors: Pavel Majer, Sykesville, MD (US); Michael Eissenstat, Frederick, MD (US); Rongjuan Lu, Gaithersburg, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 169 days.

(21) Appl. No.: 13/322,120

(22) PCT Filed: May 24, 2010

(86) PCT No.: PCT/US2010/035999
§ 371 (c)(1),
(2), (4) Date: Feb. 24, 2012

(87) PCT Pub. No.: WO2010/135748
PCT Pub. Date: Nov. 25, 2010

(65) Prior Publication Data
US 2012/0141414 A1    Jun. 7, 2012

Related U.S. Application Data

(60) Provisional application No. 61/180,809, filed on May 22, 2009.

(51) Int. Cl.
*A61K 38/00* (2006.01)
*A01N 37/18* (2006.01)

(52) U.S. Cl.
USPC .................................. 514/3.7; 514/4.3

(58) Field of Classification Search
None
See application file for complete search history.

(56) References Cited

U.S. PATENT DOCUMENTS

| 2005/0267018 | A1* | 12/2005 | Blatt et al. | 514/9 |
| 2007/0027071 | A1* | 2/2007 | Holloway et al. | 514/9 |
| 2008/0107623 | A1* | 5/2008 | D'Andrea et al. | 424/85.2 |

* cited by examiner

*Primary Examiner* — Thomas Heard
(74) *Attorney, Agent, or Firm* — Perkins Coie LLP

(57) ABSTRACT

Inhibitors of the hepatitis C virus (HCV) NS3 protease are provided. In particular, bimacrocyclic compounds and their pharmaceutical compositions for the treatment of HCV infections are provided. Methods of making the bimacrocyclic compounds and their pharmaceutical compositions, and methods of using the compounds for treating HCV infections are also provided.

20 Claims, No Drawings

BIMACROCYLIC HCV NS3 PROTEASE INHIBITORS

This application is the National Stage of International Application No. PCT/US2010/03599 filed May 24, 2010 which claims the benefit of provisional application 61/180,809, filed May 22, 2009, the contents of each of which are hereby incorporated by reference in their entireties.

FIELD OF THE TECHNOLOGY

Compounds and compositions are provided that are potent inhibitors of the hepatitis C virus (HCV) NS3 protease. In particular, bimacrocyclic compounds and pharmaceutical compositions containing the compounds are useful for treating HCV infections. Methods of making the bimacrocyclic compounds and compositions are provided, together with methods of using the compounds for treating HCV infections.

BACKGROUND

Chronic infection with HCV is a major health problem associated with liver cirrhosis, hepatocellular carcinoma and liver failure. Infection by HCV is insidious in a high proportion of chronically infected (and infectious) carriers who may not experience clinical symptoms for many years. Liver cirrhosis can ultimately lead to liver failure.

HCV is a member of the Flaviviridae family of RNA viruses that affect animals and humans. The genome is a single strand of RNA, and consists of one open reading frame that encodes for a polyprotein of about 3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. While the pathology of HCV infection affects mainly the liver, the virus is found in other cell types in the body, including peripheral blood lymphocytes.

One treatment for chronic HCV involves interferon alpha (IFN-alpha) in combination with ribavirin and this requires at least six (6) months of treatment. However, treatment of HCV with IFN-alpha has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the combination therapy of IFN-alpha and ribavirin.

Another therapy of chronic hepatitis C involves a combination of pegylated IFN-alpha plus ribavirin. However, a number of patients still experience significant side effects, primarily related to ribavirin. Ribavirin causes significant hemolysis in 10-20% of patients treated at currently recommended doses, and the drug is both teratogenic and embryotoxic. A substantial fraction of patients do not respond with a sustained reduction in viral load and there is exists a need for more effective antiviral therapy of HCV infection.

Other approaches for treatment include, for example, application of antisense oligonucleotides or ribozymes for inhibiting HCV replication. Furthermore, low-molecular weight compounds that directly inhibit HCV proteins and interfere with viral replication are potential strategies to control HCV infection. Among the viral targets, the NS3/4A protease/helicase and the NS5b RNA-dependent RNA polymerase are promising viral targets for new drugs.

One of the viral proteases, the NS3 protease, is encoded by the N-terminal region of the HCV NS3 gene. It consists of 181 amino acids and is a chymotrypsin-like serine-protease responsible for cleavage of the non-structural proteins of HCV [Bartenschlager et al., *J. Virol.* 67:3835-44.(1993)]. The hepatitis C virus encodes a serine protease involved in processing of the putative nonstructural proteins from the viral polyprotein precursor [Gallinari et al. *Biochem Biophys Res Commun* 192:399-406; (1998)]. Multiple enzymatic activities are associated with recombinant NS3 protein of hepatitis C virus [Hahm et al., *J Virol* 72:6758-6769 (1995)]. The N-terminal region of hepatitis C virus nonstructural protein 3 (NS3) is essential for stable complex formation with NS4A. [Tanji et al., *J Virol* 69:4255-4260 (1995)]. Hepatitis C virus-encoded nonstructural protein NS4A has versatile functions in viral protein processing [Tanji et al., *J Virol:*1575-1581)]. In addition, NS3 contains a tetrahedrally bound zinc atom, which appears to play a structural role [De Francesco et al., *Biochemistry* 35:13282-7 (1996)].

Models for how the protease interacts with cofactors and the substrate have identified four domains which are involved in enzyme function [Barbato et al. *J. Mol. Biol.,* 289, 371-384 (1999). The solution structure of the N-terminal proteinase domain of the HCV NS3 protein provides new insights into its activation and catalytic mechanism. [Id.]. The activation and catalytic mechanism of the enzyme appears to involve a catalytic triad, cofactor and metal binding sites and the substrate-binding pocket.

The compounds described below are potent inhibitors of the NS3 protease and are useful for inhibiting viral replication in vitro and in vivo. The compounds are useful for treating HCV infection in subjects, particularly human subjects.

SUMMARY

Inhibitors of the hepatitis C virus (HCV) NS3 protease are provided. More particularly, bimacrocyclic compounds and their pharmaceutical compositions for the treatment of HCV infections are provided. Also provided are methods of making the bimacrocyclic compounds and their pharmaceutical compositions, and methods of using the compounds for treating HCV infections.

In accordance with one embodiment, there is provided a compound represented by the formula:

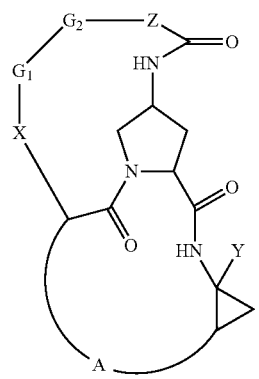

where,

Z is O, NH, or $(CH_2)_n$, where when Z is $(CH_2)_n$ then up to three methylene units of Z are optionally and independently replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NRCONR—, —S—, —SO—, —$SO_2$—, —NR—, —$SO_2$NR—, or —NR$SO_2$NR— and where up to 3 carbon atoms of Z are optionally and independently mono- or disubstituted by R1;

X is —NH$SO_2$$X^1$— or

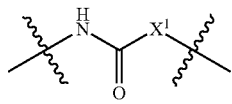

where $X^1$ is NH, O, or $(CH_2)_m$, where when $X^1$ is $(CH_2)_m$ then up to three methylene units of $X^1$ are optionally and independently replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NRCONR—, —S—, —SO—, —$SO_2$—, —NR—, —$SO_2$NR—, or —NR$SO_2$NR—, and where up to 3 carbon atoms of $X^1$ are optionally and independently mono- or disubstituted by R1;

A is optionally substituted $C_4$-$C_{10}$, alkylene, where up to three methylene units of A are optionally and independently replaced by alkenylene, alkynylene, $C_3$-$C_7$ cycloalkylene, $C_4$-$C_7$ cycloalkenylene, heterocycloalkylene, heteroaryl, —CO—, —C(S)—, —CONR—, —COO—, —COOR—, —NRCO—, —O—, —NRCONR—, —S—, —SO—, —$SO_2$—, —NR—, —$SO_2$NR—, or —NR$SO_2$NR—, where up to 3 carbon atoms of A are optionally and independently mono- or disubstituted by R1;

Y is COOH, COOR, CONHR, —COCONHR, CONH$SO_2$R, CONH($SO_2$)NRR, CONHP(O)(OR)$_2$, or CONHP(O)(OR)(NRR);

G1 and G2 independently are absent or are selected from the group consisting of monocyclic or bicyclic aryl or heteroaryl, optionally substituted by up to 3 R2 moieties, provided that at least one of G1 and G2 is present, and wherein when G1 and G2 are both present, they may be linked by a heteroatom, such as —O— or —S—;

R is H, $C_1$-$C_6$ alkyl or $C_3$-$C_6$ cycloalkyl;

R1 is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, amido, carboxyl, sulfonamido, halo, —OR, —CN, —$NO_2$, —NRR, or —$OCF_3$, R2 independently is selected from the group consisting of $C_1$-$C_{12}$ alkyl, $C_2$-$C_{12}$ alkenyl, $C_2$-$C_{12}$ alkynyl, $C_3$-$C_8$ cycloalkyl, $C_4$-$C_8$ cycloalkenyl, halo, aryl, heteroaryl, and heterocyclo, each optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —$NO_2$, —NRR, —$OCF_3$, —COOR, CONRR, COR, $SO_2$R, and SOR;

m is 0-9 and n is 0-9.

In a specific embodiment G1 and G2 both are present. In another embodiment, $X^1$ is $(CH_2)_m$ and up to 3 carbon atoms of $X^1$ are optionally and independently mono- or disubstituted by optionally substituted $C_1$-$C_{12}$ alkyl. In a further embodiment, Z is $(CH_2)_n$ and up to 3 carbon atoms of Z are optionally and independently mono- or disubstituted by optionally substituted $C_1$-$C_{12}$ alkyl. In further embodiments, $X^1$ is $(CH_2)_m$ and Z is $(CH_2)_n$ where up to 3 carbon atoms of Z and 3 carbon atoms of $X^1$ are optionally and independently mono- or disubstituted by optionally substituted $C_1$-$C_{12}$ alkyl In the compounds described above, m+n may be 3-10.

In certain embodiments at least one alkylene unit of X1 or Z is replaced by —O—, —S—, —SO—, —$SO_2$—, or —NR—. In further embodiments, at least one alkylene unit of X1 and one alkylene unit of Z is replaced by —O—, —S—, —SO—, —$SO_2$—, or —NR—.

Examples of the compounds described above include compounds having the formula

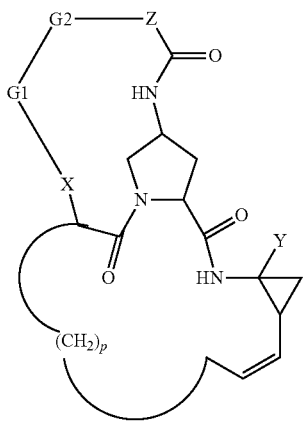

where p is 4-7;

the formula

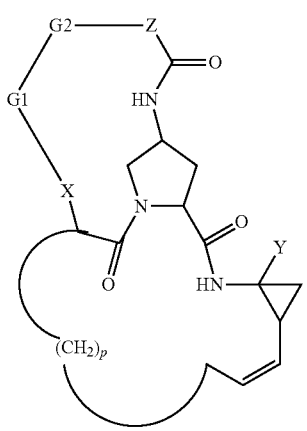

where p is 4-7 and where up to three alkylene units of $(CH_2)_p$ are independently replaced by —O—, —S—, —SO—, —$SO_2$—, or —NR—;

and the formula

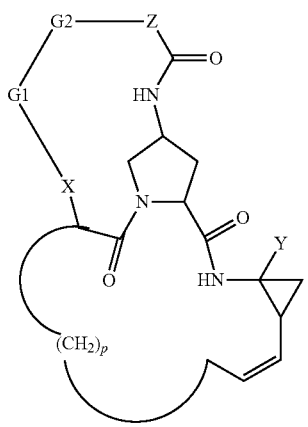

where p is 4-7 and where up to 3 carbon atoms of A are independently substituted by R1.

In the compounds described above, Y may be CONHSO$_2$R. In certain embodiments, the compound has the formula

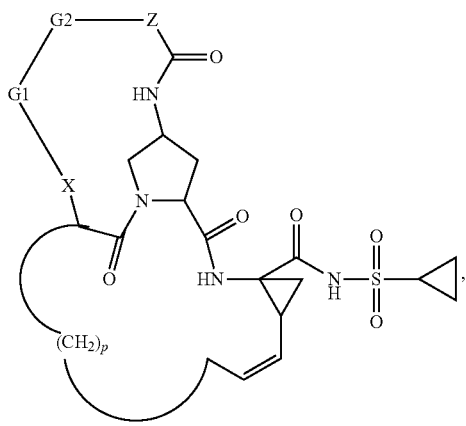

for example:

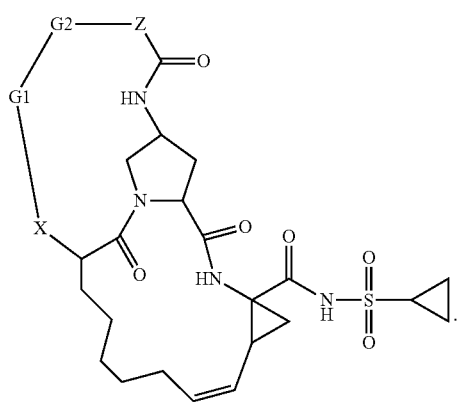

or:

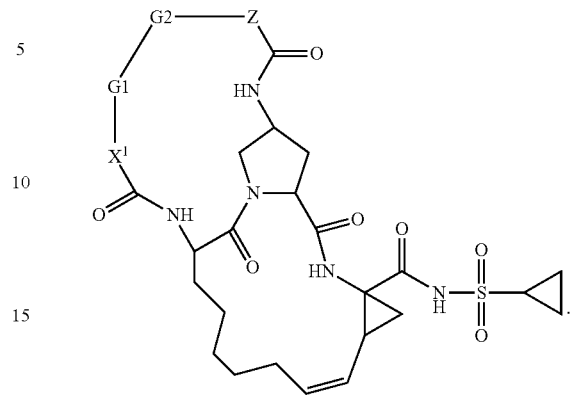

In any of these compounds, G1 and G2 each independently may be selected from the group consisting of

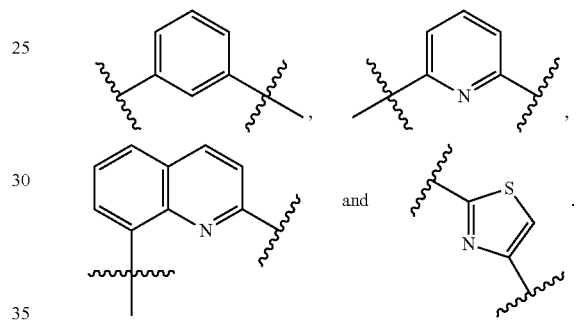

Examples of these compounds include the compounds of Table 1.

Further provided are pharmaceutical compositions contain a therapeutically effective amount of a compound as described above and a pharmaceutically acceptable diluent, adjuvant or excipient. The composition may contain additional anti-hepatitis C agent, such as interferon, interferon, ribivarin, adamantine, or an inhibitor of hepatitis C virus helicase, polymerase, metalloprotease, or IRES. In any of these compositions, an inhibitor of cytochrome p450 may also be present.

Also provided are methods of inhibiting hepatitis C virus where a patient is administered a compound or composition as described above. In these methods, a patient may also be administered an additional anti-hepatitis C agent such as interferon, interferon, ribivarin, adamantine, or an inhibitor of hepatitis C virus helicase, polymerase, metalloprotease, or IRES. The patient may also be administered an inhibitor of cytochrome p450.

Other features and advantages of the compounds, compositions, methods of treatment and the like will become apparent from the following detailed description. It should be understood, however, that the detailed description and the specific examples, while indicating specific embodiments, are given by way of illustration only and various changes and modifications will become apparent to those skilled in the art from this detailed description.

DETAILED DESCRIPTION

Compounds and compositions are provided that are potent inhibitors of the hepatitis C virus (HCV) NS3 protease. In particular, bimacrocyclic compounds and pharmaceutical compositions containing the compounds are useful for treating HCV infections. Methods of making the bimacrocyclic compounds and compositions are provided, together with methods of using the compounds for treating HCV infections.

The compounds contain an aminoproline moiety that forms part of two macrocyclic rings. The compounds can be represented by the formula I:

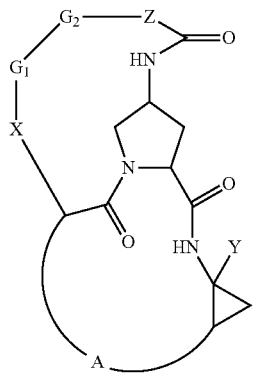

I

In these compounds Z can be O, NH, or $(CH_2)_n$. When Z is $(CH_2)_n$ then one, two or three alkylene units of Z are optionally and independently replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—.

X is —NHSO$_2$X$^1$— or

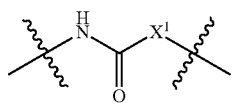

where $X^1$ is NH, O, or $(CH_2)_m$. When $X^1$ is $(CH_2)_m$, then up to three alkylene units of $X^1$ may optionally and independently be replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—.

The A moiety is optionally substituted $C_4$-$C_{10}$ alkylene, where up to three alkylene units of A are optionally and independently replaced by alkenylene, alkynylene, $C_3$-$C_7$ cycloalkylene, $C_4$-$C_7$ cycloalkenylene, heterocycloalkylene, heteroaryl, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—, where up to 3 carbon atoms of A are optionally and independently substituted by R1. Advantageously, A can contain up to 3 double bonds, which are conjugated or unconjugated, although the skilled artisan will recognize that it is possible for A to contain up to five double bonds.

The substituent Y may be COOH, COOR, CONHR, —CO-CONHR, CONHSO$_2$R, CONH(SO$_2$)NRR, CONHP(O)(OR)$_2$, or CONHP(O)(OR)(NRR).

The G1 and G2 moieties independently are absent or are selected from the group consisting of monocyclic or bicyclic aryl or heteroaryl, optionally substituted by up to 3 R2 moieties, provided that at least one of G1 and G2 is present.

R is H, $C_1$-$C_6$ alkyl or $C_3$-$C_6$ cycloalkyl.

Each R1, when present, may independently be hydrogen, optionally substituted $C_1$-$C_{12}$ alkyl, optionally substituted $C_2$-$C_{12}$ alkenyl optionally substituted $C_2$-$C_{12}$ alkynyl, optionally substituted aryl, optionally substituted aralkyl, optionally substituted cycloalkyl, optionally substituted cycloalkenyl, optionally substituted heterocycle, optionally substituted heteroaryl, amido, carboxyl, sulfonamido, halo, —OR, —CN, —NO$_2$, —NRR, or —OCF$_3$.

Each R2, when present, may independently be selected from the group consisting of $C_1$-$C_{12}$, alkyl, $C_2$-$C_{12}$ alkenyl, $C_2$-$C_{12}$ alkynyl, $C_3$-$C_8$ cycloalkyl, $C_4$-$C_8$ cycloalkenyl, aryl, heteroaryl, and heterocyclo, each optionally substituted by up to three substituents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —NO$_2$, —NRR, —OCF$_3$, —COOR, CONRR, COR, SO$_2$R, and SOR.

m is 0-9 and n is 0-9.

In some embodiments, only one of G1 and G2 is present, while in others, both G1 and G2 are present.

In certain embodiments. Z is $(CH_2)_n$ and Z is $(CH_2)_n$. Advantageously, m+n is 3-10.

In specific embodiments, at least one alkylene unit of X1 or Z is replaced by —O—, —S—, —SO—, —SO$_2$—, or —NR—. One alkylene unit of X1 and one alkylene unit of Z may be replaced by —O—, —S—, —SO—, —SO$_2$—, or —NR—.

Advantageously, the compound may have the formula II:

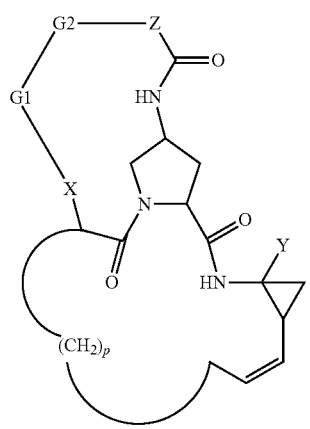

II where p is 4-7 and the remaining substituents are as defined above. In these compounds, 0, 1, 2, or 3 alkylene units of $(CH_2)_p$ may independently be replaced by —O—, —S—, —SO—, —SO$_2$—, or —NR—, and 0, 1, 2, or 3 carbon atoms of A are independently substituted by R1.

In any of these compounds, Y advantageously may be CONHSO$_2$R. In such instances, R advantageously may be cyclopropyl and the compounds have the formula III:

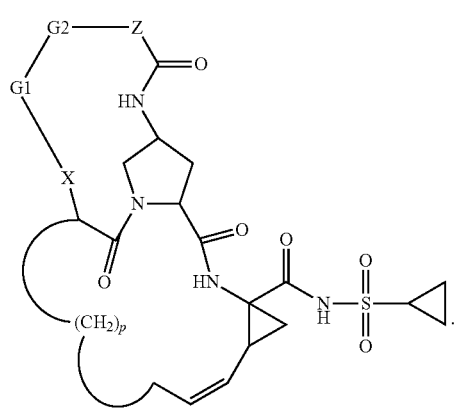

where the variable substituents are as defined above.

In specific embodiments, the compounds may be represented by the formula IV

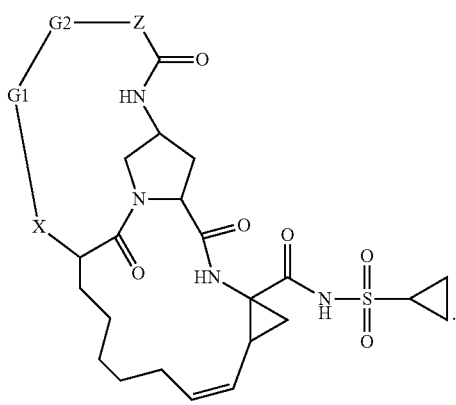

where the substituents are as defined above.

In other specific embodiments, the compounds may be represented by the formula

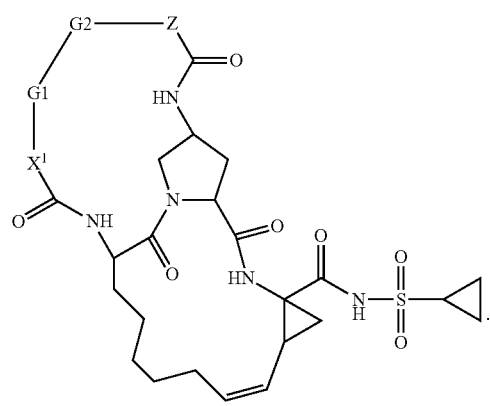

where the substituents are as defined above.

In any of these compounds G1 and G2 advantageously are each independently selected from the group consisting of

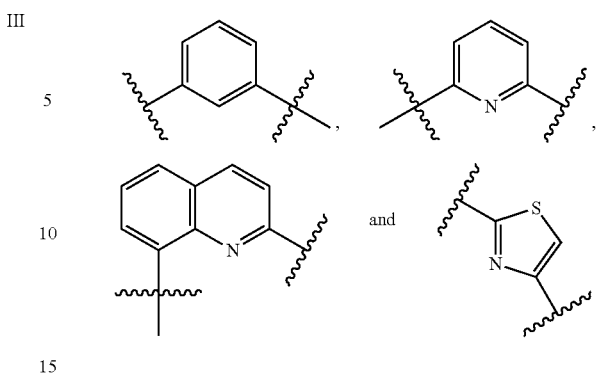

Specific examples of compounds are provided below in Table 1, but the skilled artisan will recognize that these merely exemplify the compounds, and do not limit the scope of the compounds having a formula as described above. In particular, Table 2 below shows other exemplary types of compound, and the skilled artisan will recognize that the compounds encompass each moiety exemplified in Table 1:

TABLE 1

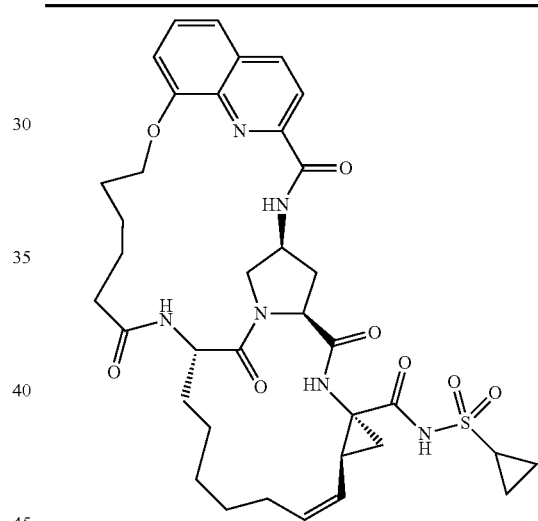

1

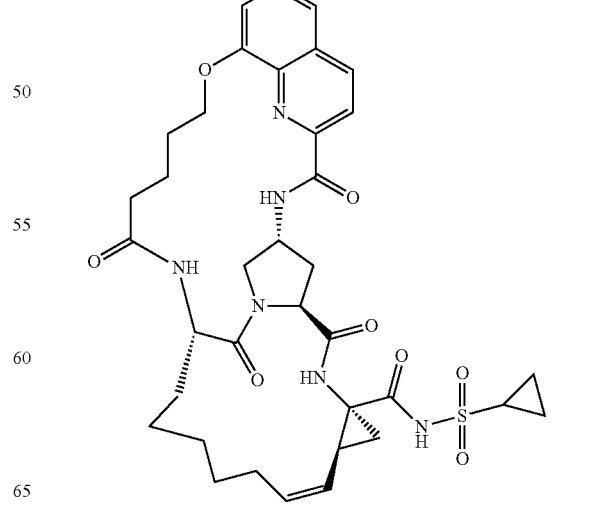

2

TABLE 1-continued
3
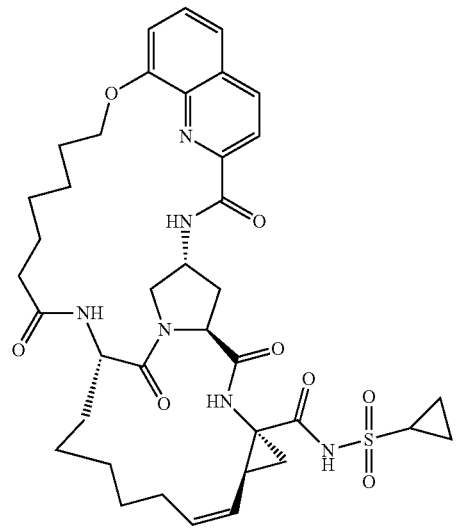 [SMILES: O=C1CCCCCCOc2cccc3ccc(nc23)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
4
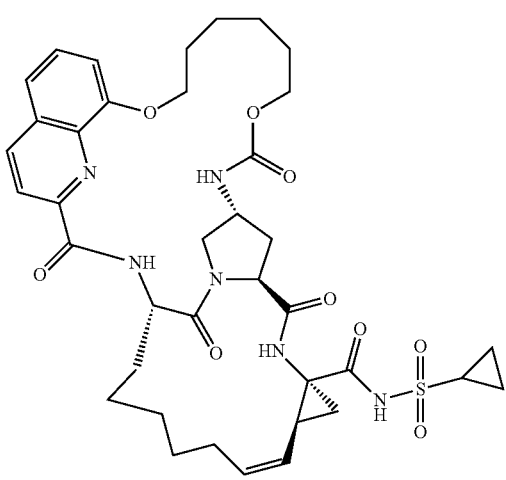 [SMILES: O=C1N[C@@H]2C[C@H]3C(=O)N[C@]4(C(=O)NS(=O)(=O)C5CC5)C[C@H]4/C=C\CCCCC[C@H](NC(=O)c4ccc5cccc(c5n4)OCCCCCCO1)C(=O)N3C2]
5
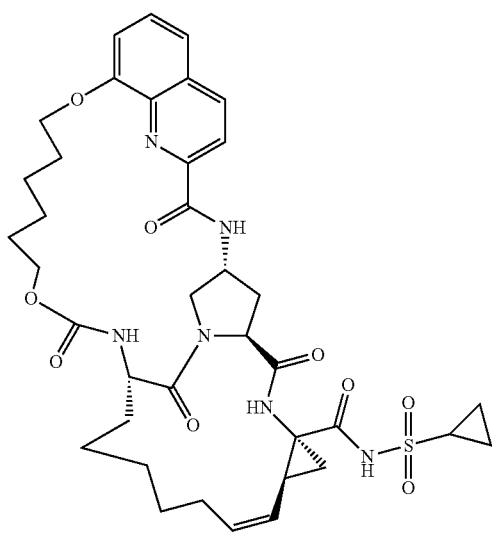 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2ccc3cccc(c3n2)OCCCCCCO1]
TABLE 1-continued
6
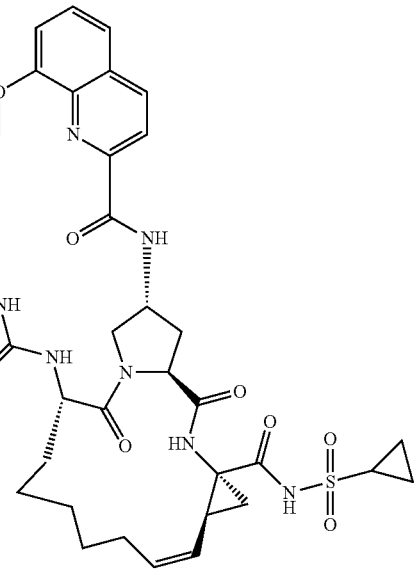
7
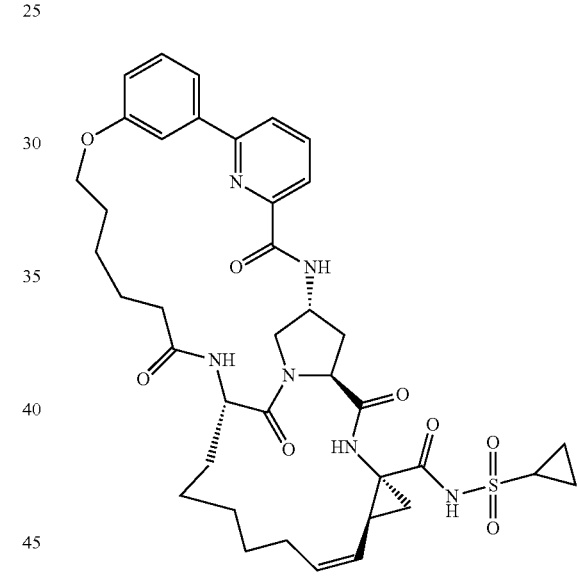
8
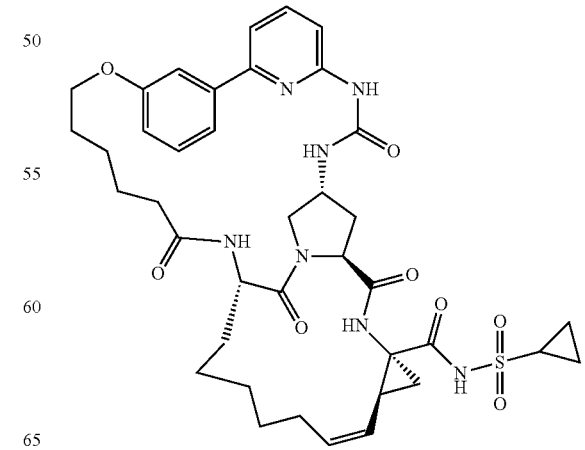

TABLE 1-continued
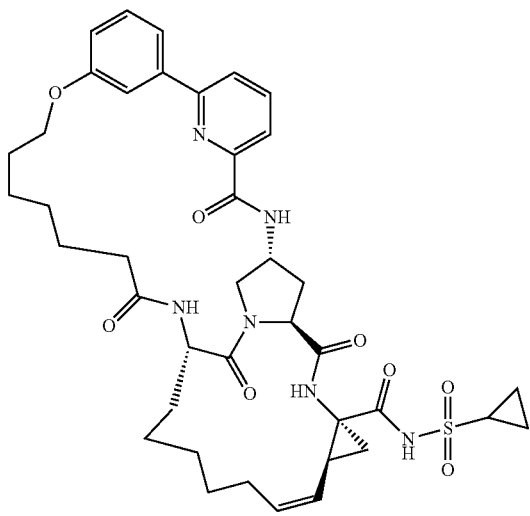 [SMILES: O=C1CCCCCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
9
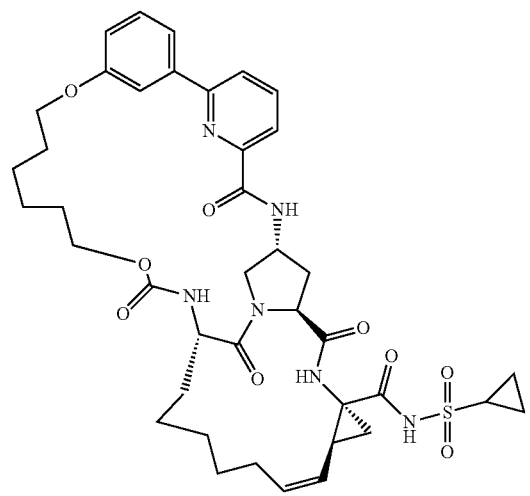 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cccc(c2)OCCCCCCO1]
10
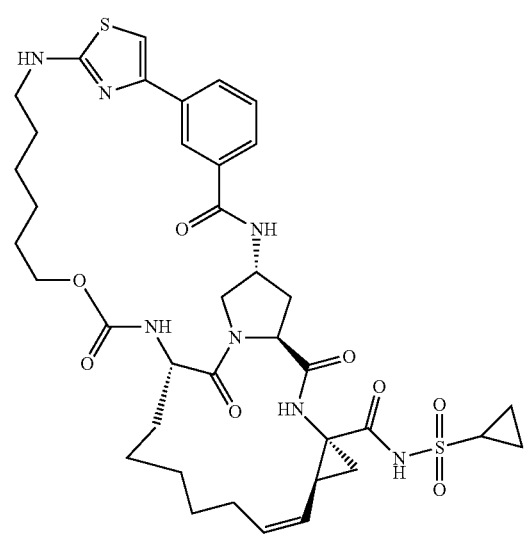 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(c2)-c2csc(n2)NCCCCCCO1]
11
TABLE 1-continued
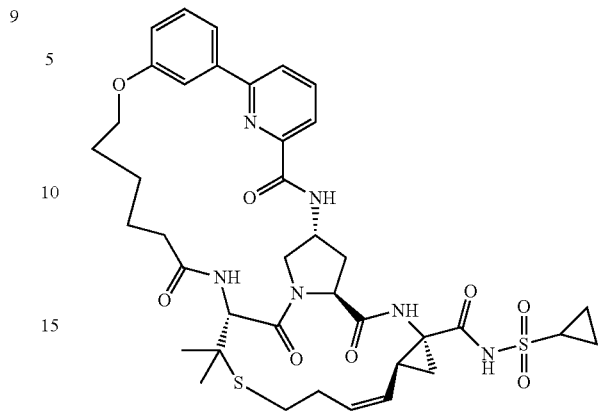
12
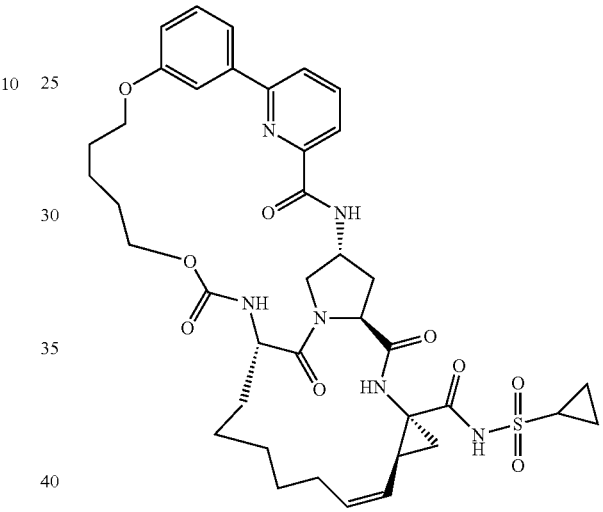
13
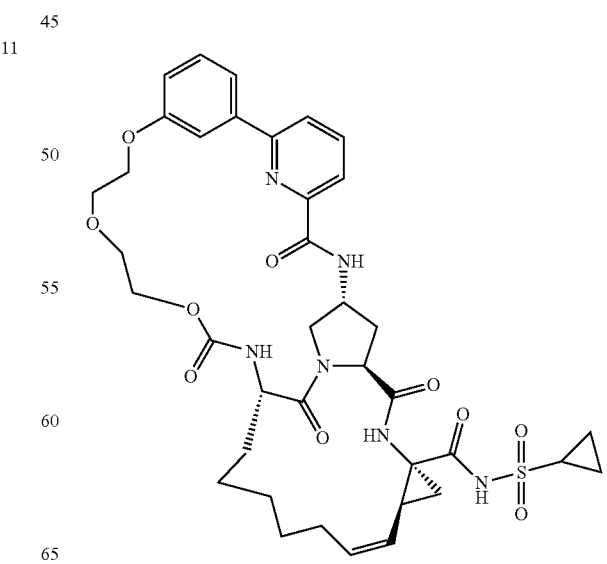
14

TABLE 1-continued
15
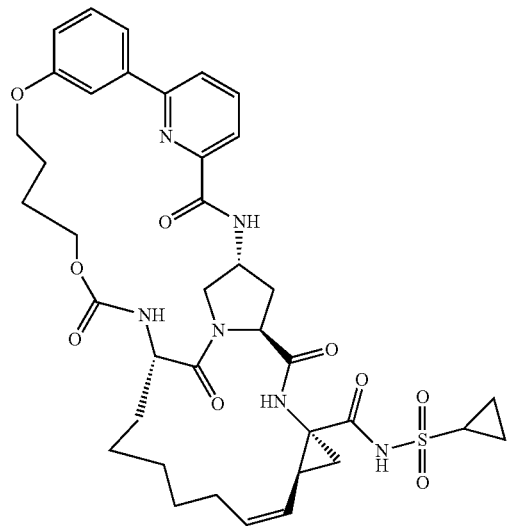 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cccc(c2)OCCCCO1]
16
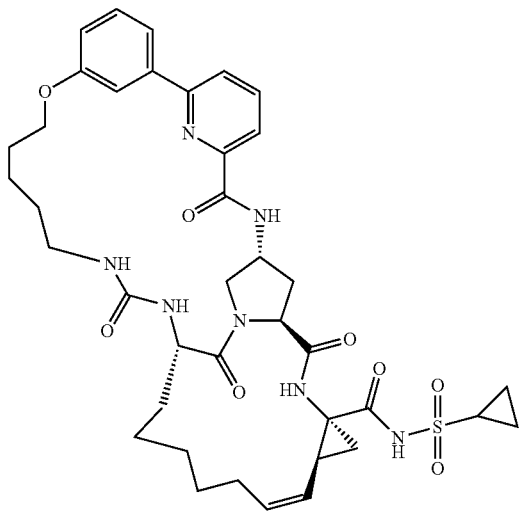 [SMILES: O=C1NCCCCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
17
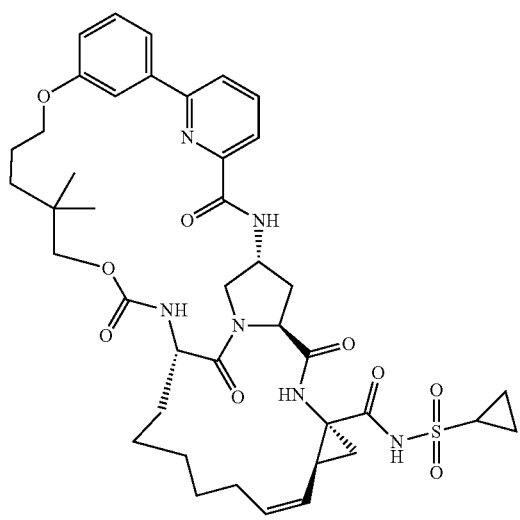 [SMILES: CC1(C)CCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](NC(=O)OC1)C(=O)N3C2]
18
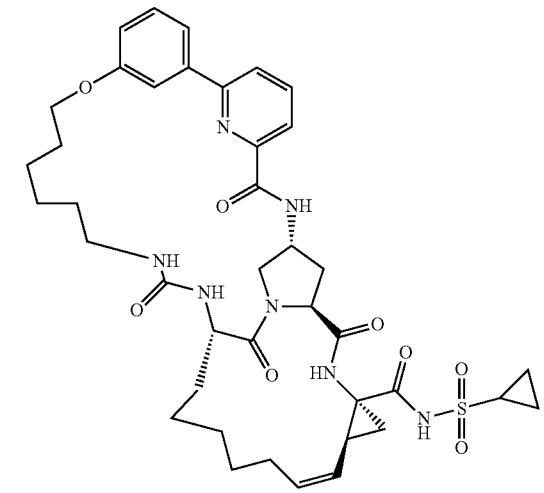 [SMILES: O=C1NCCCCCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
19
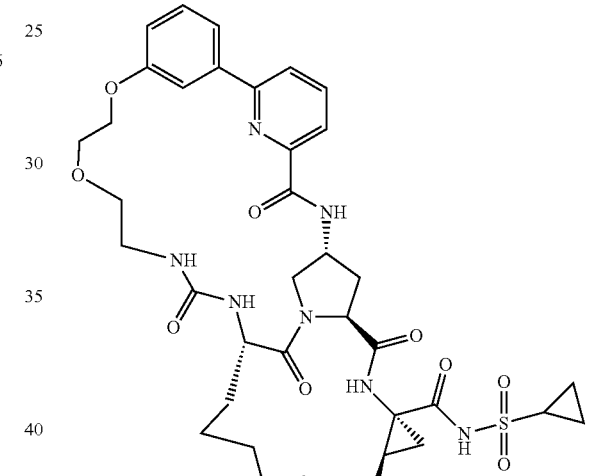
20
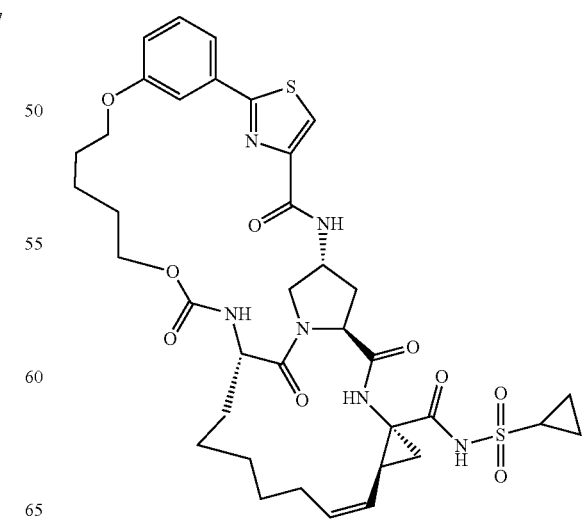

TABLE 1-continued
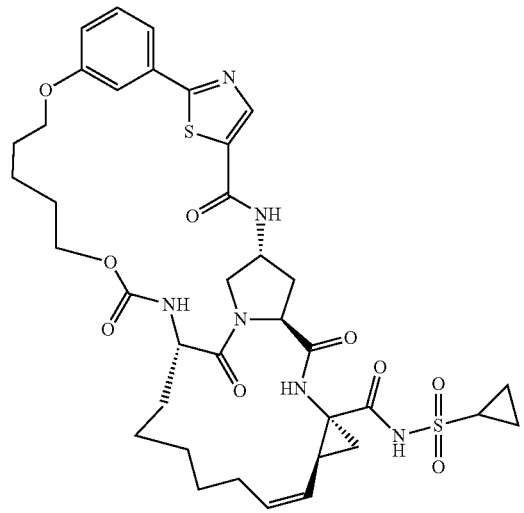 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)C2=CN=C(S2)c2cccc(c2)OCCCCCO1]
21
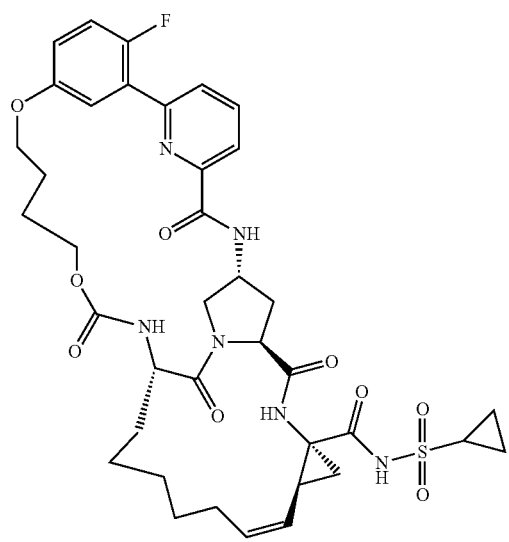 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cc(ccc2F)OCCCCO1]
22
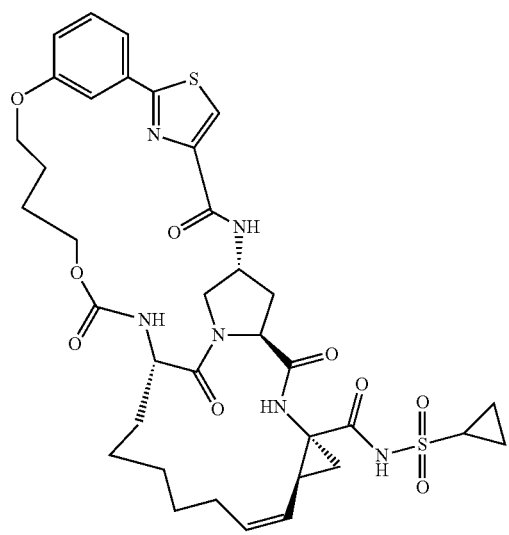 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2csc(n2)-c2cccc(c2)OCCCCO1]
23
TABLE 1-continued
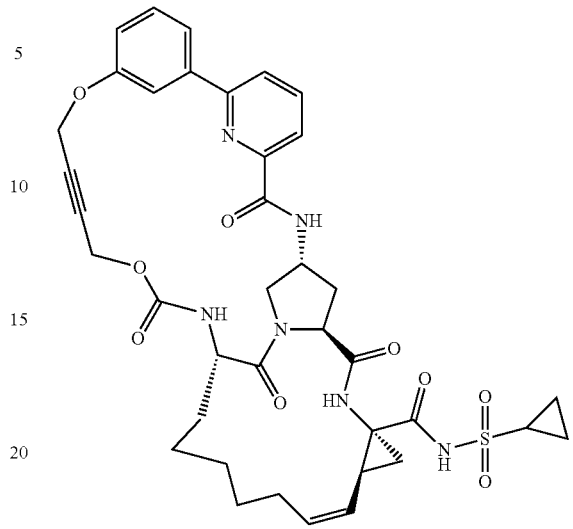
24
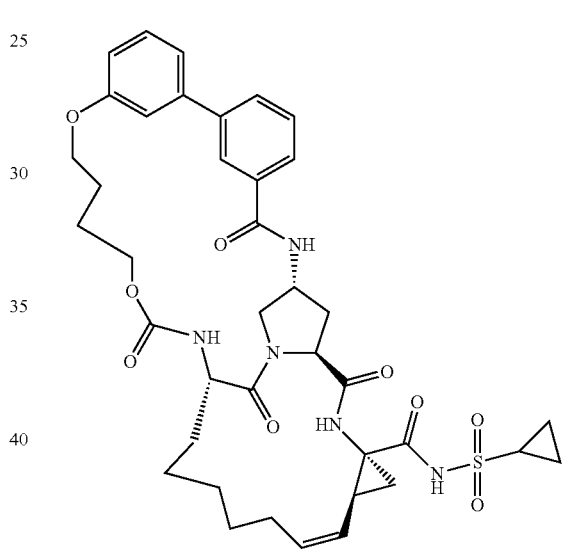
25
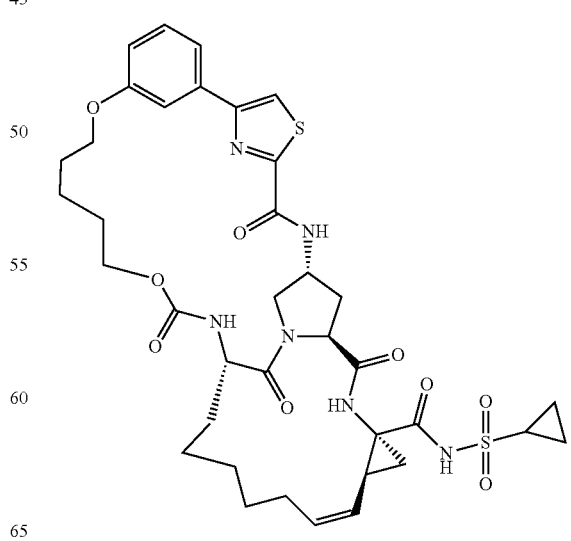
26

TABLE 1-continued
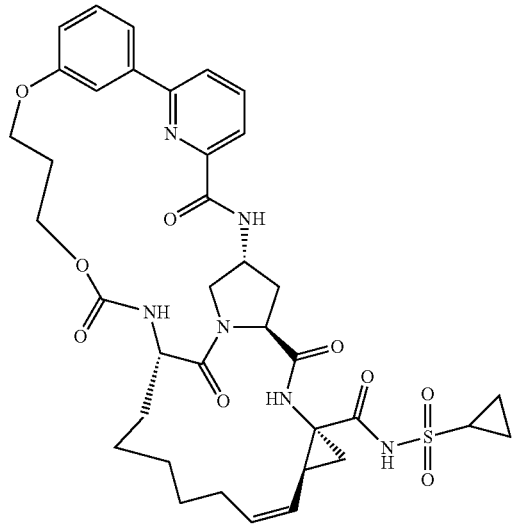 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cccc(c2)OCCCO1]
27
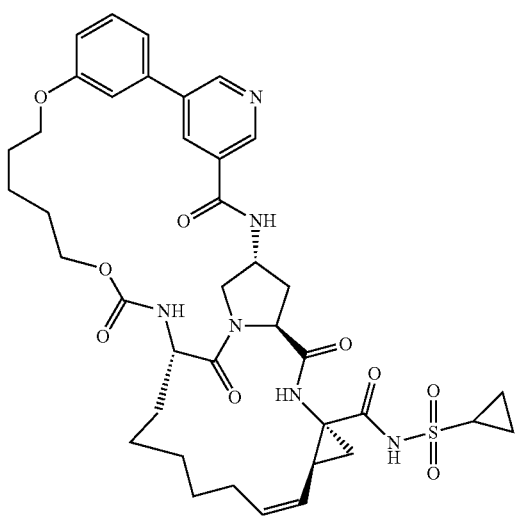 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cncc(c2)-c2cccc(c2)OCCCCCO1]
28
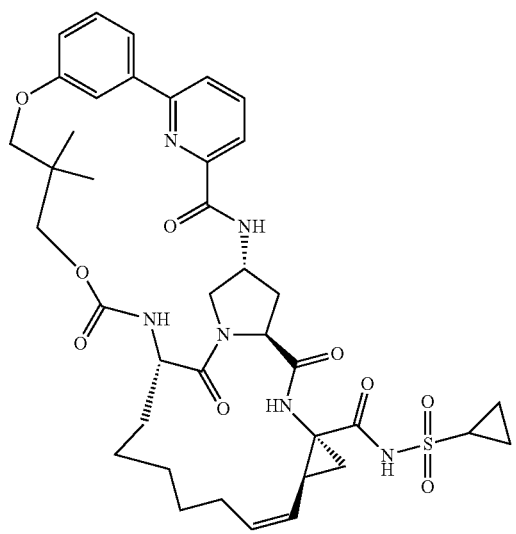 [SMILES: CC1(C)COC(=O)N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cccc(c2)OC1]
29
TABLE 1-continued
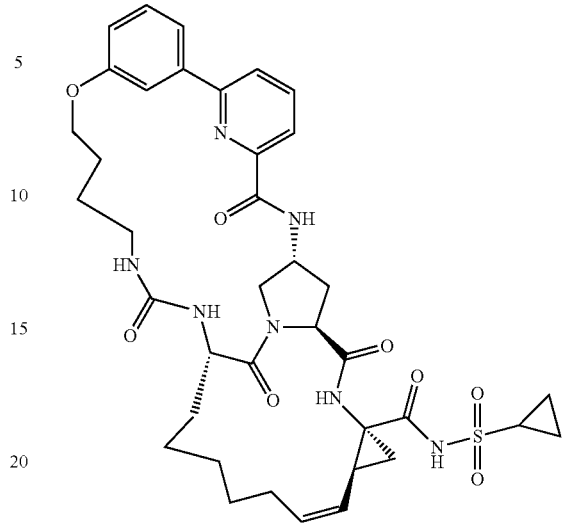
30
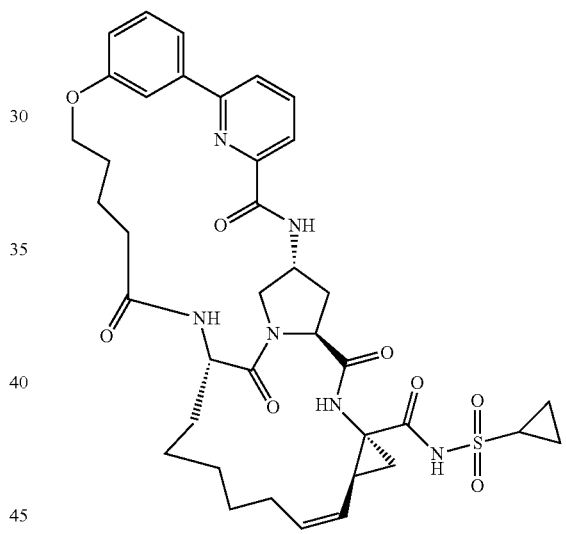
31
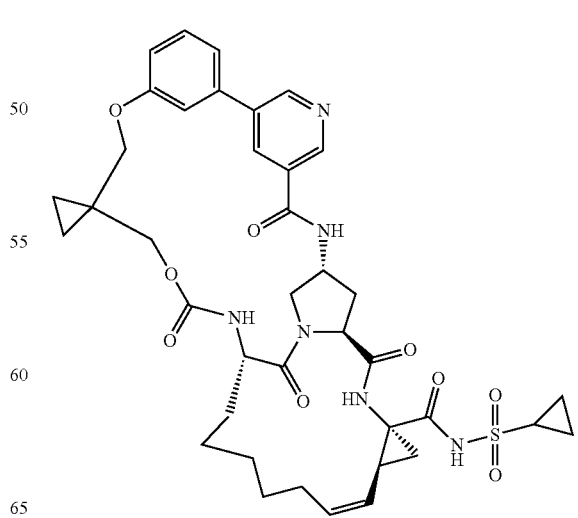
32

TABLE 1-continued
33
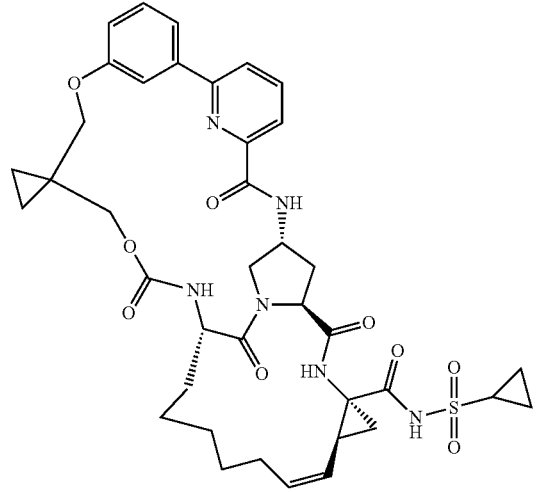 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cccc(n2)-c2cccc(c2)OCC2(CC2)CO1]
34
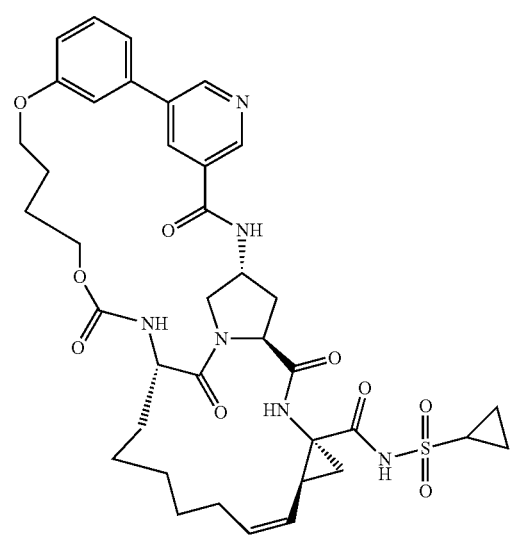 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)c2cncc(c2)-c2cccc(c2)OCCCCO1]
35
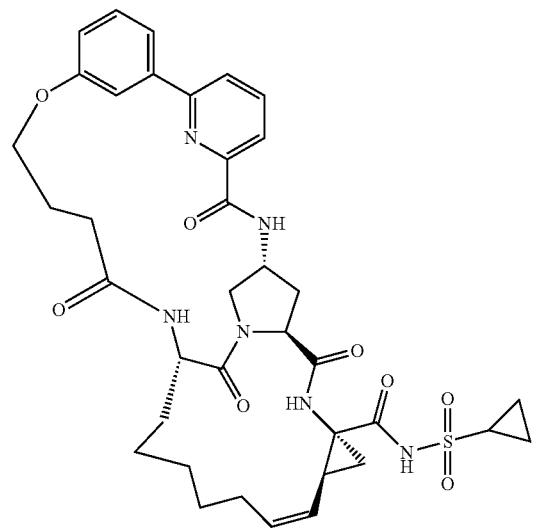 [SMILES: O=C1CCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
TABLE 1-continued
36
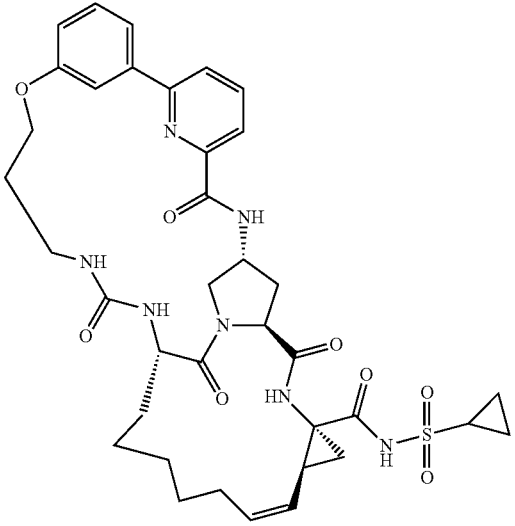 [SMILES: O=C1NCCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]
37
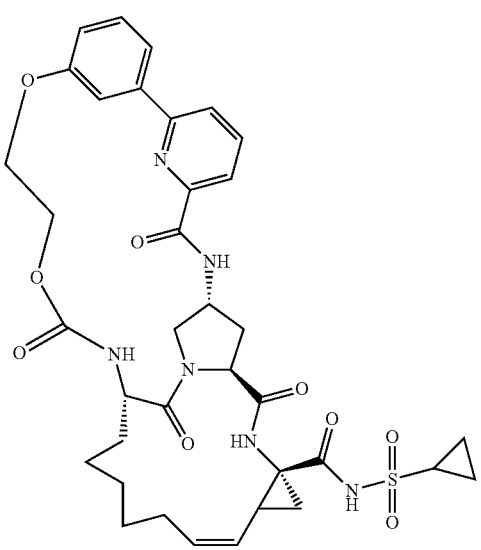
38
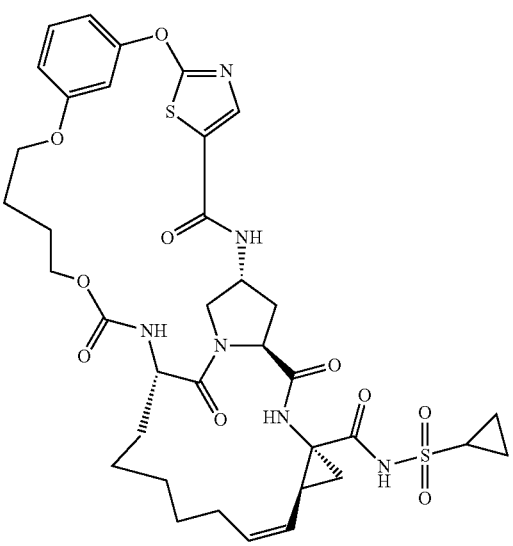 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)NC(=O)C2=CN=C(Oc3cccc(c3)OCCCCO1)S2]

TABLE 1-continued

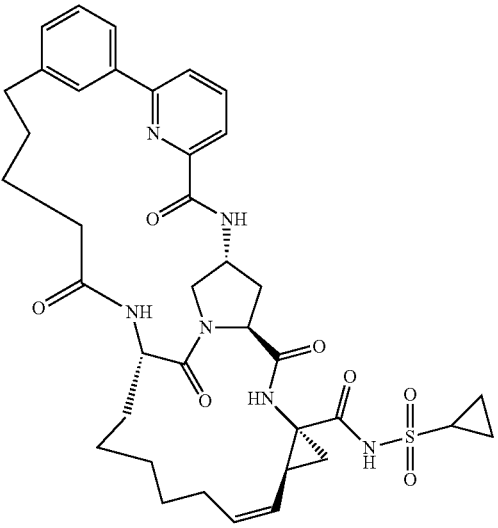 [SMILES: O=C1CCCCc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]

39

TABLE 2

| | Z | X | X¹ | A | Y | G1 | G2 | n or m |
|---|---|---|---|---|---|---|---|---|
| 1 | O | —NHSO$_2$X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 2 | NH | —NHSO$_2$X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 3 | bond (n = 0) | —NHSO$_2$X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n = 0 m is 0-9 |
| 4 | —(CH$_2$)$_n$ | —NHSO$_2$X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 5 | —(CH$_2$)$_n$ with 1 or 2 —CH$_2$- groups replaced by —O— | —NHSO$_2$X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 6 | O | —NHC(O)X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 7 | NH | —NHC(O)X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 8 | bond (n = 0) | —NHC(O)X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | 0 m is 0-9 |
| 9 | —(CH$_2$)$_n$ | —NHC(O)X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 10 | —(CH$_2$)$_n$ with 1 or 2 —CH$_2$- groups replaced by —O— | —NHC(O)X¹ | X¹ is (CH$_2$)$_m$ | A is alkenylene with one C=C bond | —CONH(SO$_2$)NRR | absent or monocyclic aryl or heteroaryl | monocyclic or bicyclic aryl or heteroaryl | n is 0-9 m is 0-9 |
| 11 | O | —NHSO$_2$X¹ | X¹ is (CH$_2$)$_m$ | A is alkenylene with two C=C bonds | —CONH(SO$_2$)NRR | absent or monocyclic aryl or heteroaryl | monocyclic or bicyclic aryl or heteroaryl | n is 0-9 m is 0-9 |

TABLE 2-continued

| | Z | X | X¹ | A | Y | G1 | G2 | n or m |
|---|---|---|---|---|---|---|---|---|
| 12 | NH | —NHSO₂X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 13 | bond (n = 0) | —NHSO₂X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n = 0 m is 0-9 |
| 14 | —(CH₂)ₙ | —NHSO₂X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 15 | —(CH₂)ₙ with 1 or 2 —CH₂- groups replaced by —O— | —NHSO₂X¹ | X¹ is (CH₂)ₘ | A is alkenylene with two C═C bondsA is alkenylene with two C═C bonds | —CONH(SO₂)NRR | absent or monocyclic aryl or heteroaryl | monocyclic or bicyclic aryl or heteroaryl | n is 0-9 m is 0-9 |
| 16 | O | —NHC(O)X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 17 | NH | —NHC(O)X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 18 | bond (n = 0) | —NHC(O)X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0 m is 0-9 |
| 19 | —(CH₂)ₙ | —NHC(O)X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 20 | —(CH₂)ₙ with 1 or 2 —CH₂- groups replaced by —O— | —NHC(O)X¹ | X¹ is (CH₂)ₘ | A is alkenylene with two C═C bonds | —CONH(SO₂)NRR | absent or monocyclic aryl or heteroaryl | monocyclic or bicyclic aryl or heteroaryl | n is 0-9 m is 0-9 |
| 21 | O | —NHSO₂X¹ | X¹ is (CH₂)ₘ | A is alkenylene with one C═C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 22 | NH | —NHSO₂X¹ | X¹ is (CH₂)ₘ | A is alkenylene with one C═C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 23 | bond (n = 0) | —NHSO₂X¹ | X¹ is (CH₂)ₘ | A is alkenylene with one C═C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n = 0 m is 0-9 |
| 24 | —(CH₂)ₙ | —NHSO₂X¹ | X¹ is (CH₂)ₘ | A is alkenylene with one C═C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 25 | —(CH₂)ₙ with 1 or 2 —CH₂- groups replaced by —O— | —NHSO₂X¹ | X¹ is (CH₂)ₘ | A is alkenylene with one C═C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 26 | O | —NHC(O)X¹ | X¹ is (CH₂)ₘ | A is alkenylene with one C═C bond | —CO(SO₂)NR where R is a 3-5 member cycloalkyl or a 3 member cycloalkyl moiety | absent, or monocyclic aryl or heteroaryl | monocyclic or bicyclic aryl or heteroaryl | n is 0-9 m is 0-9 |

TABLE 2-continued

| | Z | X | $X^1$ | A | Y | G1 | G2 | n or m |
|---|---|---|---|---|---|---|---|---|
| 27 | NH | —NHC(O)$X^1$ | $X^1$ is $(CH_2)_m$ | A is alkenylene with one C=C bond | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 28 | bond (n = 0) | —NHC(O)$X^1$ | $X^1$ is $(CH_2)_m$ | A is alkenylene with one C=C bond | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0 m is 0-9 |
| 29 | —(CH$_2$)$_n$ | —NHC(O)$X^1$ | $X^1$ is $(CH_2)_m$ | A is alkenylene with one C=C bond | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 30 | —(CH$_2$)$_n$ with 1 or 2 —CH$_2$- groups replaced by —O— | —NHC(O)$X^1$ | $X^1$ is $(CH_2)_m$ | A is alkenylene with one C=C bond | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 31 | O | —NHSO$_2$$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 32 | NH | —NHSO$_2$$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 33 | bond (n = 0) | —NHSO$_2$$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n = 0 m is 0-9 |
| 34 | —(CH$_2$)$_n$ | —NHSO$_2$$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 35 | —(CH$_2$)$_n$ with 1 or 2 —CH$_2$- groups replaced by —O— | —NHSO$_2$$X^1$ | $X^1$ is $(CH_2)_m$ | A is alkenylene with two C=C bondsA is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 36 | O | —NHC(O)$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 37 | NH | —NHC(O)$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 38 | bond (n = 0) | —NHC(O)$X^1$ | $X^1$ is $(CH_2)_m$ | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0 m is 0-9 |
| 39 | —(CH$_2$)$_n$ | —NHC(O)$X^1$ | $X^1$ is $(CH_2)_m$ | A is alkenylene with two C=C bonds | —CO(SO$_2$)NR where R is a 3-5 member cycloalkyl or a 3 | absent or monocyclic aryl or heteroaryl | monocyclic or bicyclic aryl or heteroaryl | n is 0-9 m is 0-9 |

TABLE 2-continued

| | Z | X | X¹ | A | Y | G1 | G2 | n or m |
|---|---|---|---|---|---|---|---|---|
| 40 | —(CH₂)ₙ with 1 or 2 —CH₂- groups replaced by —O— | —NHC(O)X¹ | X¹ is (CH₂)ₘ | A is alkenylene with two C=C bonds | member cycloalkyl moiety —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 m is 0-9 |
| 41 | O | —NHSO₂X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 42 | NH | —NHSO₂X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 43 | bond (n = 0) | —NHSO₂X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n = 0 m is 0-9 |
| 44 | —(CH₂)ₙ | —NHSO₂X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 45 | —(CH₂)ₙ with 1 or 2 —CH₂- groups replaced by —O— | —NHSO₂X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 46 | O | —NHC(O)X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 47 | NH | —NHC(O)X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 48 | bond (n = 0) | —NHC(O)X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0 m is 0-9 |
| 49 | —(CH₂)ₙ | —NHC(O)X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 50 | —(CH₂)ₙ with 1 or 2 —CH₂- groups replaced by —O— | —NHC(O)X¹ | X¹ is (CH₂)ₘ | A is alkenylene with one C=C bond | —CONH(SO₂)NRR | monocyclic or bicyclic aryl or heteroaryl | absent or monocyclic aryl or heteroaryl | n is 0-9 m is 0-9 |
| 51 | O | —NHSO₂X¹ | X¹ is (CH₂)ₘ | A is alkenylene with two C=C bonds | —CONH(SO₂)NRR | monocyclic or bicyclic aryl or heteroaryl | absent or monocyclic aryl or heteroaryl | n is 0-9 m is 0-9 |
| 52 | NH | —NHSO₂X¹ | X¹ is (CH₂)ₘ | A is alkenylene with two C=C bonds | —CONH(SO₂)NRR | monocyclic or bicyclic aryl or heteroaryl | absent or monocyclic aryl or heteroaryl | n is 0-9 m is 0-9 |
| 53 | bond (n = 0) | —NHSO₂X¹ | X¹ is (CH₂)ₘ | A is alkenylene with two C=C bonds | —CONH(SO₂)NRR | monocyclic or bicyclic aryl or heteroaryl | absent or monocyclic aryl or heteroaryl | n = 0 m is 0-9 |
| 54 | —(CH₂)ₙ | —NHSO₂X¹ | X¹ is (CH₂)ₘ | A is alkenylene with two C=C bonds | —CONH(SO₂)NRR | monocyclic or bicyclic aryl or heteroaryl | absent or monocyclic aryl or heteroaryl | n is 0-9 m is 0-9 |
| 55 | —(CH₂)ₙ with 1 or 2 —CH₂- groups replaced by —O— | —NHSO₂X¹ | X¹ is (CH₂)ₘ | A is alkenylene with two C=C bondsA is alkenylene with two C=C bonds | —CONH(SO₂)NRR | monocyclic or bicyclic aryl or heteroaryl | absent or monocyclic aryl or heteroaryl | n is 0-9 m is 0-9 |
| 56 | O | —NHC(O)X¹ | X¹ is (CH₂)ₘ | A is alkenylene | —CONH(SO₂)NRR | monocyclic or bicyclic | absent or monocyclic | n is 0-9 |

TABLE 2-continued

| | Z | X | X¹ | A | Y | G1 | G2 | n or m |
|---|---|---|---|---|---|---|---|---|
| 57 | NH | —NHC(O)X¹ | X¹ is (CH$_2$)$_m$ | A is alkenylene with two C═C bonds | —CONH(SO$_2$)NRR | monocyclic or bicyclic aryl or heteroaryl | absent or monocyclic aryl or heteroaryl | n is 0-9 m is 0-9 |
| 58 | bond (n = 0) | —NHC(O)X¹ | X¹ is (CH$_2$)$_m$ | A is alkenylene with two C═C bonds | —CONH(SO$_2$)NRR | monocyclic or bicyclic aryl or heteroaryl | absent or monocyclic aryl or heteroaryl | n is 0 m is 0-9 |
| 59 | —(CH$_2$)$_n$ | —NHC(O)X¹ | X¹ is (CH$_2$)$_m$ | A is alkenylene with two C═C bonds | —CONH(SO$_2$)NRR | monocyclic or bicyclic aryl or heteroaryl | absent or monocyclic aryl or heteroaryl | n is 0-9 m is 0-9 |
| 60 | —(CH$_2$)$_n$ with 1 or 2 —CH$_2$- groups replaced by —O— | —NHC(O)X¹ | X¹ is (CH$_2$)$_m$ | A is alkenylene with two C═C bonds | —CONH(SO$_2$)NRR | monocyclic or bicyclic aryl or heteroaryl | absent or monocyclic aryl or heteroaryl | n is 0-9 m is 0-9 |
| 61 | O | —NHSO$_2$X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 62 | NH | —NHSO$_2$X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 63 | bond (n = 0) | —NHSO$_2$X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n = 0 m is 0-9 |
| 64 | —(CH$_2$)$_n$ | —NHSO$_2$X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 65 | —(CH$_2$)$_n$ with 1 or 2 —CH$_2$- groups replaced by —O— | —NHSO$_2$X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 66 | O | —NHC(O)X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 67 | NH | —NHC(O)X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 68 | bond (n = 0) | —NHC(O)X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0 m is 0-9 |
| 68 | —(CH$_2$)$_n$ | —NHC(O)X¹ | X¹ is (CH$_2$)$_m$ | A is alkenylene with one C═C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 70 | —(CH$_2$)$_n$ with 1 or 2 —CH$_2$- groups | —NHC(O)X¹ | X¹ is (CH$_2$)$_m$ | A is alkenylene with one C═C bond | —CO(SO$_2$)NR where R is a 3-5 member cycloalkyl or a 3 | monocyclic or bicyclic aryl or heteroaryl | absent or monocyclic aryl or heteroaryl | n is 0-9 m is 0-9 |

TABLE 2-continued

| | Z | X | X¹ | A | Y | G1 | G2 | n or m |
|---|---|---|---|---|---|---|---|---|
| 71 | replaced by —O— O | —NHSO₂X¹ | X¹ is (CH₂)ₘ | A is alkenylene with two C═C bonds | member cycloalkyl moiety —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 72 | NH | —NHSO₂X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 73 | bond (n = 0) | —NHSO₂X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n = 0 m is 0-9 |
| 74 | —(CH₂)ₙ | —NHSO₂X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 75 | —(CH₂)ₙ with 1 or 2 —CH₂- groups replaced by —O— | —NHSO₂X¹ | X¹ is (CH₂)ₘ | A is alkenylene with two C═C bondsA is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 76 | O | —NHC(O)X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 77 | NH | —NHC(O)X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 78 | bond (n = 0) | —NHC(O)X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0 m is 0-9 |
| 79 | —(CH₂)ₙ | —NHC(O)X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 80 | —(CH₂)ₙ with 1 or 2 —CH₂- groups replaced by —O— | —NHC(O)X¹ | X¹ is (CH₂)ₘ | A is alkenylene with two C═C bonds | —CO(SO₂)NR where R is a 3-5 member cycloalkyl or a 3 member cycloalkyl moiety | monocyclic or bicyclic aryl or heteroaryl | absent or monocyclic aryl or heteroaryl | n is 0-9 m is 0-9 |
| 81 | O | —NHSO₂X¹ | X¹ is NH or O | A is alkenylene with one C═C bond | —CONH(SO₂)NRR | absent or monocyclic aryl or heteroaryl | monocyclic or bicyclic aryl or heteroaryl | n is 0-9 |
| 82 | NH | —NHSO₂X¹ | X¹ is NH or O | A is alkenylene with one C═C bond | —CONH(SO₂)NRR | absent or monocyclic aryl or heteroaryl | monocyclic or bicyclic aryl or heteroaryl | n is 0-9 |
| 83 | bond (n = 0) | —NHSO₂X¹ | X¹ is NH or O | A is alkenylene with one C═C bond | —CONH(SO₂)NRR | absent or monocyclic aryl or heteroaryl | monocyclic or bicyclic aryl or heteroaryl | n is 0 |
| 84 | —(CH₂)ₙ | —NHSO₂X¹ | X¹ is NH or | A is alkenylene | —CONH(SO₂)NRR | absent or monocyclic | monocyclic or bicyclic | n is 0-9 |

TABLE 2-continued

| | Z | X | X¹ | A | Y | G1 | G2 | n or m |
|---|---|---|---|---|---|---|---|---|
| 85 | —(CH$_2$)$_n$ with 1 or 2 —CH$_2$- groups replaced by —O— | —NHSO$_2$X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0-9 |
| 86 | O | —NHC(O)X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0-9 |
| 87 | NH | —NHC(O)X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0-9 |
| 88 | bond (n = 0) | —NHC(O)X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0 |
| 89 | —(CH$_2$)$_n$ | —NHC(O)X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0-9 |
| 90 | —(CH$_2$)$_n$ with 1 or 2 —CH$_2$- groups replaced by —O— | —NHC(O)X¹ | X¹ is NH or O | A is alkenylene with one C=C bond | —CONH(SO$_2$)NRR | absent or monocyclic aryl or heteroaryl | monocyclic or bicyclic aryl or heteroaryl | n is 0-9 |
| 91 | O | —NHSO$_2$X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 92 | NH | —NHSO$_2$X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 93 | bond (n = 0) | —NHSO$_2$X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0 |
| 94 | —(CH$_2$)$_n$ | —NHSO$_2$X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 95 | —(CH$_2$)$_n$ with 1 or 2 —CH$_2$- groups replaced by —O— | —NHSO$_2$X¹ | X¹ is NH or O | A is alkenylene with two C=C bondsA is alkenylene with two C=C bonds | —CONH(SO$_2$)NRR | absent or monocyclic aryl or heteroaryl | monocyclic or bicyclic aryl or heteroaryl | n is 0-9 |
| 96 | O | —NHC(O)X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 97 | NH | —NHC(O)X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 98 | bond (n = 0) | —NHC(O)X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0 |
| 99 | —(CH$_2$)$_n$ | —NHC(O)X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 100 | —(CH$_2$)$_n$ with 1 or 2 —CH$_2$- groups replaced by —O— | —NHC(O)X¹ | X¹ is NH or O | A is alkenylene with two C=C bonds | —CONH(SO$_2$)NRR | absent or monocyclic aryl or heteroaryl | monocyclic or bicyclic aryl or heteroaryl | n is 0-9 |
| 101 | O | —NHSO$_2$X¹ | X¹ is NH or O | A is alkenylene | —CO(SO$_2$)NR where R is a 3-5 | absent or monocyclic | monocyclic or bicyclic | n is 0-9 |

TABLE 2-continued

| | Z | X | X¹ | A | Y | G1 | G2 | n or m |
|---|---|---|---|---|---|---|---|---|
| | | | O | with one C=C bond | member cycloalkyl or a 3 member cycloalkyl moiety | aryl or heteroaryl | aryl or heteroaryl | |
| 102 | NH | —NHSO₂X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 103 | bond (n = 0) | —NHSO₂X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0 |
| 104 | —(CH₂)ₙ | —NHSO₂X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 105 | —(CH₂)ₙ with 1 or 2 —CH₂- groups replaced by —O— | —NHSO₂X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 106 | O | —NHC(O)X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 107 | NH | —NHC(O)X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 108 | bond (n = 0) | —NHC(O)X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0 |
| 109 | —(CH₂)ₙ | —NHC(O)X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 110 | —(CH₂)ₙ with 1 or 2 —CH₂- groups replaced by —O— | —NHC(O)X¹ | X¹ is NH or O | A is alkenylene with one C=C bond | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 111 | O | —NHSO₂X¹ | X¹ is NH or O | A is alkenylene with two C=C bonds | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 112 | NH | —NHSO₂X¹ | X¹ is NH or O | A is alkenylene with two C=C bonds | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0-9 |
| 113 | bond (n = 0) | —NHSO₂X¹ | X¹ is NH or O | A is alkenylene with two C=C bonds | —CO(SO₂)NR where R is a 3-5 member cycloalkyl or a 3 member cycloalkyl moiety | absent or monocyclic aryl or heteroaryl | monocyclic or bicyclic aryl or heteroaryl | n is 0 |
| 114 | —(CH₂)ₙ | —NHSO₂X¹ | X¹ is NH or O | A is alkenylene | —CO(SO₂)NR where R is a 3-5 | absent or monocyclic | monocyclic or bicyclic | n is 0-9 |

TABLE 2-continued

| | Z | X | X¹ | A | Y | G1 | G2 | n or m |
|---|---|---|---|---|---|---|---|---|
| | | | O | with two C=C bonds | member cycloalkyl or a 3 member cycloalkyl moiety | aryl or heteroaryl | aryl or heteroaryl | |
| 115 | —(CH$_2$)$_n$ with 1 or 2 —CH$_2$- groups replaced by —O— | —NHSO$_2$X¹ | X¹ is NH or O | A is alkenylene with two C=C bondsA is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 |
| 116 | O | —NHC(O)X¹ | X¹ is NH or O | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 |
| 117 | NH | —NHC(O)X¹ | X¹ is NH or O | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 |
| 118 | bond (n = 0) | —NHC(O)X¹ | X¹ is NH or O | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0 |
| 119 | —(CH$_2$)$_n$ | —NHC(O)X¹ | X¹ is NH or O | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 |
| 120 | —(CH$_2$)$_n$ with 1 or 2 —CH$_2$- groups replaced by —O— | —NHC(O)X¹ | X¹ is NH or O | A is alkenylene with two C=C bonds | —CO(SO$_2$)NR where R is a 3-5 member cycloalkyl or a 3 member cycloalkyl moiety | absent or monocyclic aryl or heteroaryl | monocyclic or bicyclic aryl or heteroaryl | n is 0-9 |
| 121 | O | —NHSO$_2$X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 122 | NH | —NHSO$_2$X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 123 | bond (n = 0) | —NHSO$_2$X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0 |
| 124 | —(CH$_2$)$_n$ | —NHSO$_2$X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 125 | —(CH$_2$)$_n$ with 1 or 2 —CH$_2$- groups replaced by —O— | —NHSO$_2$X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 126 | O | —NHC(O)X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 127 | NH | —NHC(O)X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0-9 |
| 128 | bond (n = 0) | —NHC(O)X¹ | X¹ is NH or O | A is alkenylene with one C=C bond | —CONH(SO$_2$)NRR | monocyclic or bicyclic aryl or heteroaryl | absent or monocyclic aryl or heteroaryl | n is 0 |
| 129 | —(CH$_2$)$_n$ | —NHC(O)X¹ | X¹ is NH or O | A is alkenylene | —CONH(SO$_2$)NRR | monocyclic or bicyclic | absent or monocyclic | n is 0-9 |

TABLE 2-continued

| | Z | X | X¹ | A | Y | G1 | G2 | n or m |
|---|---|---|---|---|---|---|---|---|
| 130 | —(CH$_2$)$_n$ with 1 or 2 —CH$_2$- groups replaced by —O— | —NHC(O)X¹ | O X¹ is NH or O | with one C=C bond A is alkenylene with one C=C bond | —CONH(SO$_2$)NRR | aryl or heteroaryl monocyclic or bicyclic aryl or heteroaryl | aryl or heteroaryl absent or monocyclic aryl or heteroaryl | n is 0-9 |
| 131 | O | —NHSO$_2$X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 132 | NH | —NHSO$_2$X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 133 | bond (n = 0) | —NHSO$_2$X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0 |
| 134 | —(CH$_2$)$_n$ | —NHSO$_2$X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 135 | —(CH$_2$)$_n$ with 1 or 2 —CH$_2$- groups replaced by —O— | —NHSO$_2$X¹ | X¹ is NH or O | A is alkenylene with two C=C bondsA is alkenylene with two C=C bonds | —CONH(SO$_2$)NRR | monocyclic or bicyclic aryl or heteroaryl | absent or monocyclic aryl or heteroaryl | n is 0-9 |
| 136 | O | —NHC(O)X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 137 | NH | —NHC(O)X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 138 | bond (n = 0) | —NHC(O)X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0 |
| 139 | —(CH$_2$)$_n$ | —NHC(O)X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 140 | —(CH$_2$)$_n$ with 1 or 2 —CH$_2$- groups replaced by —O— | —NHC(O)X¹ | X¹ is NH or O | A is alkenylene with two C=C bonds | —CONH(SO$_2$)NRR | monocyclic or bicyclic aryl or heteroaryl | absent or monocyclic aryl or heteroaryl | n is 0-9 |
| 141 | O | —NHSO$_2$X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 142 | NH | —NHSO$_2$X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 143 | bond (n = 0) | —NHSO$_2$X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0 |
| 144 | —(CH$_2$)$_n$ | —NHSO$_2$X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |

TABLE 2-continued

| | Z | X | X¹ | A | Y | G1 | G2 | n or m |
|---|---|---|---|---|---|---|---|---|
| 145 | —(CH$_2$)$_n$ with 1 or 2 —CH$_2$- groups replaced by —O— | —NHSO$_2$X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 146 | O | —NHC(O)X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 147 | NH | —NHC(O)X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 148 | bond (n = 0) | —NHC(O)X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0 |
| 149 | —(CH$_2$)$_n$ | —NHC(O)X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 150 | —(CH$_2$)$_n$ with 1 or 2 —CH$_2$- groups replaced by —O— | —NHC(O)X¹ | X¹ is NH or O | A is alkenylene with one C=C bond | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 151 | O | —NHSO$_2$X¹ | X¹ is NH or O | A is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 152 | NH | —NHSO$_2$X¹ | X¹ is NH or O | A is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 153 | bond (n = 0) | —NHSO$_2$X¹ | X¹ is NH or O | A is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0 |
| 154 | —(CH$_2$)$_n$ | —NHSO$_2$X¹ | X¹ is NH or O | A is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 155 | —(CH$_2$)$_n$ with 1 or 2 —CH$_2$- groups replaced by —O— | —NHSO$_2$X¹ | X¹ is NH or O | A is alkenylene with two C=C bondsA is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 156 | O | —NHC(O)X¹ | X¹ is NH or O | A is alkenylene with two C=C bonds | —CO(SO$_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 157 | NH | —NHC(O)X¹ | X¹ is NH or O | A is alkenylene with two C=C bonds | —CO(SO$_2$)NR where R is a 3-5 member cycloalkyl or a 3 | monocyclic or bicyclic aryl or heteroaryl | absent or monocyclic aryl or heteroaryl | n is 0-9 |

TABLE 2-continued

| | Z | X | $X^1$ | A | Y | G1 | G2 | n or m |
|---|---|---|---|---|---|---|---|---|
| 158 | bond (n = 0) | —NHC(O)$X^1$ | $X^1$ is NH or O | A is alkenylene with two C=C bonds | member cycloalkyl moiety —CO($SO_2$)NR where R is a 3-5 member cycloalkyl or a 3 member cycloalkyl moiety | monocyclic or bicyclic aryl or heteroaryl | absent or monocyclic aryl or heteroaryl | n is 0 |
| 159 | —($CH_2$)$_n$ | —NHC(O)$X^1$ | $X^1$ is NH or O | A is alkenylene with two C=C bonds | —CO($SO_2$)NR where R is a 3-5 member cycloalkyl or a 3 member cycloalkyl moiety | monocyclic or bicyclic aryl or heteroaryl | absent or monocyclic aryl or heteroaryl | n is 0-9 |
| 160 | —($CH_2$)$_n$ with 1 or 2 —$CH_2$- groups replaced by —O— | —NHC(O)$X^1$ | $X^1$ is NH or O | A is alkenylene with two C=C bonds | —CO($SO_2$)NR where R is a 3-5 member cycloalkyl or a 3 member cycloalkyl moiety | monocyclic or bicyclic aryl or heteroaryl | absent or monocyclic aryl or heteroaryl | n is 0-9 |

The compounds may be formulated in pharmaceutical compositions in ways that are known in the art, as described in more detail below. Briefly, the compositions contain a therapeutically effective amount of a compound as described above, together with a pharmaceutically acceptable diluent, adjuvant or excipient. In such compositions, the HCV NS3 protease inhibitor as described above may be the only pharmacologically active compound, or the composition may contain one or more additional pharmacologically active compounds. The additional compound(s) may be one or more anti-hepatitis C agent, including, but not limited to interferon-α2a, interferon-α2b, ribavirin, adamantine, an inhibitor of HCV helicase, an inhibitor of HCV RNA polymerase (NS5B), an HCV NS2 metalloprotease inhibitor, or an inhibitor of the HCV internal ribosome entry site (IRES). The additional compound(s) may also be one or more inhibitors of a cytochrome p450, advantageously one or more inhibitors of cytochrome p450 enzymes that degrade the HCV NS3 protease inhibitor and/or that degrade one or more additional pharmacologically active compounds. Such cytochrome inhibitors are often described as "boosters" and suitable booster molecules are known in the art and are described in more detail below.

The NS3 protease inhibitors and compositions containing the inhibitors can be used for inhibiting HCV replication in vitro and in vivo, and for treating a hepatitis C virus infection in a subject, advantageously a human subject. Briefly, a compound as described above, or a composition containing the compound as described above, is administered to a subject suffering from HCV infection. The compound or composition contains an amount of one or more compounds as described above that is effective for suppressing replication of the HCV to a desired degree. Advantageously, the viral replication is suppressed to a degree that provides therapeutic benefit, for example to a degree that the immune system of the subject can contain or eliminate the virus. In particular, viral replication may be suppressed sufficiently that provides a negative qualitative HCV RNA measurement at a defined endpoint after the end of treatment, e.g. 24 weeks after the end of treatment.

The compounds and/or compositions containing the compounds may also be used in treatment regimens where an additional agent is separately administered to the subject. The additional agent may be, for example interferon-α2a, interferon-α2b, ribavirin, adamantine, an inhibitor of HCV helicase, an inhibitor of HCV RNA polymerase (NS5B), an HCV NS2 metalloprotease inhibitor, or an inhibitor of the HCV internal ribosome entry site (IRES).

Preparation of the Protease Inhibitors

Scheme 1 shows an exemplary synthetic pathway that may be used to prepare the compounds as described above. "Pg" as used herein, refers to a protecting group. Suitable protecting groups for moieties such as amines, alcohols, acids, etc. are known to one of ordinary skill in the art. Each starting material compound, intermediate compound or end product may include one or more such protecting groups to allow for selective functional group transformations such as those that are known to a person of ordinary skill in the art. See for example, (Greene, T. W., et al., *Protective Groups in Organic Synthesis*, John Wiley & Sons, $3^{rd}$ edition 1999). Methods for protection and deprotection of functional groups are well known in the art.

As illustrated in scheme 1, a compound such as 110 can be prepared starting from known commercially available compounds using known functional group transformations. Compound 110 can be differentially protected using suitable protecting groups. A series of synthetic steps can lead to compound 120. Compound 120 can further be transformed to compound 130. A cyclization reaction such as for example, a ring closing metathesis can lead to compound 140. A subsequent cyclization reaction can be used to obtain the final bimacrocyclic compound 160 via intermediate compounds such as compound 150.

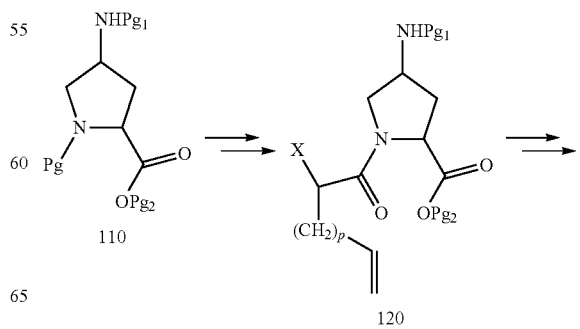

Scheme 1

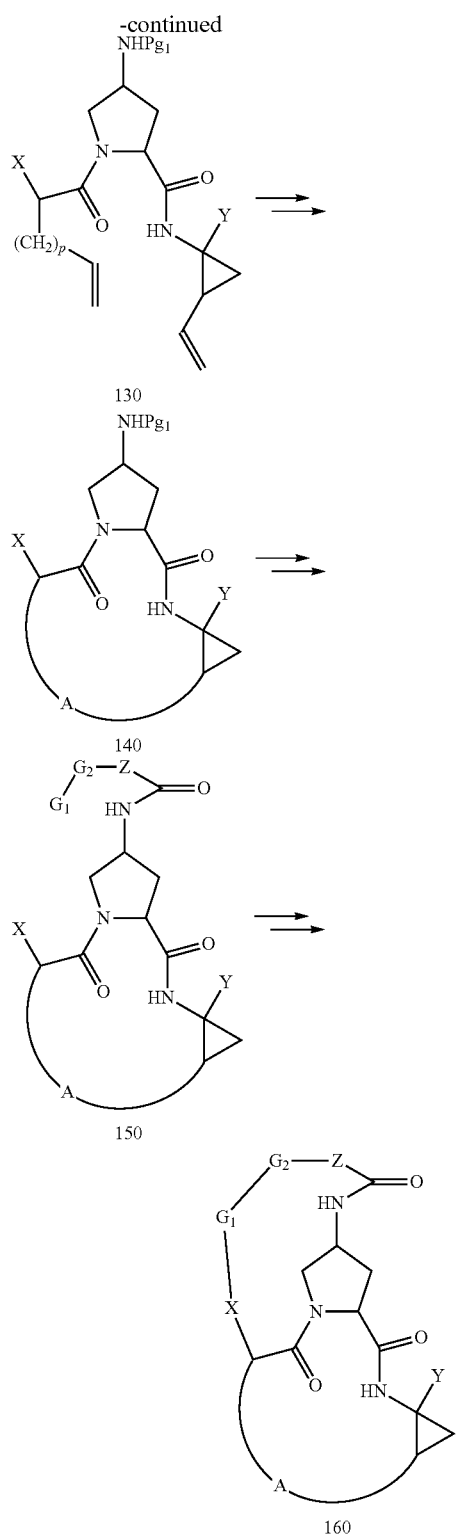

The skilled artisan will recognize that synthetic, schemes also may be used in which, for example, the order of assembly of the macrocylic rings is reversed, or where substituents are introduced at different points within the scheme. A variety of synthetic pathways are available to a person of skill in the art to synthesize the starting materials and/or intermediates employed in the present technology. For example, syntheses described in US 20080107623, US 20050153877, US 20050267018, WO 200537214 and WO 2004072243 can be utilized and are herein incorporated by reference in their entirety.

Definitions

The term "alkyl", alone or in combination with any other term, refers to a straight-chain or branched-chain saturated aliphatic hydrocarbon radical containing the specified number of carbon atoms, or where no number is specified, advantageously from 1 to about 12 or 1 to 15 carbon atoms. Examples of alkyl radicals include, but are not limited to methyl, ethyl, n-propyl, isopropyl, n-butyl, isobutyl, sec-butyl, tert-butyl, pentyl, isoamyl, n-hexyl and the like.

The term "alkenyl", alone or in combination with, any other term, refers to a straight-chain or branched-chain mono- or poly-unsaturated aliphatic hydrocarbon radical containing the specified number of carbon atoms, or where no number is specified, advantageously from 2-6 or 2-10 carbon atoms. Alkenyl groups include all possible E and Z isomers unless specifically stated otherwise. Examples of alkenyl radicals include, but are not limited to: ethenyl, propenyl, isopropenyl, butenyl, isobutenyl, pentenyl, hexenyl, hexadienyl and the like.

The term "alkynyl," alone or in combination with any other term, refers to a straight-chain or branched-chain hydrocarbon radical having one or more triple bonds containing the specified number of carbon atoms, or where no number is specified, advantageously from 2 to about 10 carbon atoms. Examples of alkynyl radicals include, but are not limited to: ethynyl, propynyl, propargyl, butynyl, pentynyl and the like.

The terms "alkylene", "alkenylene" and alkynylene" as a group or part of a group refer to the groups "alkyl", "alkenyl" and "alkynyl" respectively, when they are divalent, i.e. attached at two atoms.

The term "alkoxy" refers to an alkyl ether radical, where the term "alkyl" is as defined above. Examples of suitable alkyl ether radicals include, but are not limited to: methoxy, ethoxy, n-propoxy, isopropoxy, n-butoxy, isobutoxy, sec-butoxy, tert-butoxy and the like.

The term "aralkoxy" refers to an aralkyl ether radical, where the term "aralkyl" is as defined herein. An example is the benzyloxy radical.

The terms "alkylamino" or "dialkylamino" include amino radicals substituted by one or two alkyl groups, where the term "alkyl" is defined above, and the alkyl groups can be the same or different. Examples of suitable alkylamino and dialkylamino radicals include, but are not limited to: methylamino, ethylamino, isopropylamino, dimethylamino, methylethylamino, ethylbutylamino and the like.

The term "hydroxyalkyl" refers to an alkyl radical as defined above in which one of the hydrogen atoms is replaced by a hydroxy group. Examples of suitable hydroxyalkyl radicals include, but are not limited to: hydroxymethyl, 2-hydroxypropyl and the like.

The term "alkoxyalkyl" refers to an alkyl radical as defined above in which one of the hydrogen atoms is replaced by an alkoxy radical as defined above.

The terms "aminoalkyl", "alkylaminoalkyl" or "dialkylaminoalkyl" refers to an alkyl radical as defined above in which one of the hydrogen atoms is replaced by an amino or "alkylamino" or "dialkylamino" radical as defined above.

The term "halo" or "halogen" includes fluorine, chlorine, bromine or iodine.

The term "haloalkyl" refers to alkyl groups with one or more of its hydrogens replaced by halogens.

The term "thioalkyl" includes alkyl radicals having at least one sulfur atom, where alkyl has the significance given above. An example of a thioalkyl is $CH_3SCH_2$. The definition also encompasses the corresponding sulfoxide and sulfone of this thioalkyl: $CH_3S(O)CH_2$ and $CH_3S(O)_2CH_2$ respectively. Unless expressly stated to the contrary, the terms "—$SO_2$—" and "—$S(O)_2$—" as used herein refer to sulfone or sulfone derivatives (i.e., both appended groups linked to the S), and not a sulfinate ester.

The terms "carboalkoxy" or "alkoxycarbonyl" refers to alkyl esters of a carboxylic acid. Examples of "carboalkoxy" or "alkoxycarbonyl" radicals include, but are not limited to ethoxycarbonyl (or carboethoxy), Boc (or t-butoxycarbonyl), Cbz (or benzyloxycarbonyl) and the like.

The terms "carboaralkoxy" or "aralkoxycarbonyl" refers to aralkyl esters of a carboxylic acid. Examples of "carboaralkoxy" or "aralkoxylcarbonyl" radicals include, but are not limited to Cbz (or benzyloxycarbonyl) and the like.

The term "alkanoyl" refers to acyl radicals derived from an alkanecarboxylic acid. Examples of alkanoyl radicals include, but are not limited to: acetyl, propionyl, isobutyryl and the like.

The term "aryl," alone or in combination with any other term, refers to a carbocyclic aromatic radical (such as phenyl or naphthyl), preferably from 6-15 carbon atoms, and more preferably from 6-10 carbon atoms, and optionally substituted with one or more substituents selected from alkyl, alkoxy, (for example methoxy), nitro, halo, amino, mono or dialkylamino, carboalkoxy, cyano, thioalkyl, alkanoyl, carboxylate, alkanesulfonyl, and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, refers to alkyl radicals as defined above in which one or more hydrogen atoms is replaced by an aryl radical as defined above. Examples of aralkyl radicals include, but are not limited to benzyl, 2-phenylethyl and the like.

The term "aralkanoyl" refers to acyl radicals derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, (1-naphthyl)acetyl, 4-methoxyhydrocinnamoyl, and the like.

The term "aroyl" refers to acyl radicals derived from an aromatic carboxylic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "arylsulfonyl" refers to sulfonyl radicals derived from an aromatic sulfonic acid such as benzenesulfonyl, 4-chlorobenzenesulfonyl, 1-naphthalenesulfonyl, 2-naphthalenesulfonyl, and the like.

The term "carbocycle" refers to a non-aromatic stable 3- to 8-membered carbon ring which can be saturated, mono-unsaturated or poly-unsaturated. The carbocycle can be attached at any endocyclic carbon atom which results in a stable structure. Preferred carbocycles have 5-7 carbons.

The term "cycloalkyl", alone or in combination, refers to alkyl radicals which contain from about 3 to about 8 carbon atoms and are cyclic. Examples of such cycloalkyl radicals include cyclopropyl, cyclobutyl, cyclopentyl, cyclohexyl and the like.

The term "cycloalkenyl" alone or in combination refers to alkenyl radicals as defined above which contain about 3-8 carbon atoms and are cyclic.

The term "cycloalkylalkyl" refers to alkyl radicals as defined above which are substituted by a cycloalkyl radical containing from about 3 to about 8, preferably from about 3 to about 6, carbon atoms.

The term "heterocyclyl" or "heterocyclo" or "heterocycloalkyl" refers to a stable 3-7 membered monocyclic heterocycle or 8-11 membered bicyclic heterocycle which is either saturated or partially unsaturated, and which can be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, aryl, alkylsulfonyl, arylsulfonyl, or aralkyl or on a tertiary nitrogen atom (i.e., +N—) by oxido and which is attached via a carbon atom or a heteroatom as valency permits. Each heterocycle consists of one or more carbon atoms and from one to four heteroatoms selected from the group consisting of nitrogen, oxygen and sulfur. As used herein, the terms "nitrogen and sulfur heteroatoms" include oxidized forms of nitrogen and sulfur, and the quaternized form of any basic nitrogen. Preferred heterocycles include 5-7 membered monocyclic heterocycles, and 8-10 membered bicyclic heterocycles. Examples of such groups imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroaryl" refers to stable 5-6 membered monocyclic or 8-11 membered bicyclic or 13-16 membered tricyclic aromatic heterocycles where heterocycles is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiadiazyl, oxathiolyl, acridinyl, phenanthridinyl, and benzocinnolinyl.

The term "heterocycloalkylalkyl" refers to an alkyl radical as defined above which is substituted by a heterocycloalkyl radical as defined above.

The term "heteroaralkyl" alone or in combination, refers to alkyl radicals as defined above in which one or more hydrogen atom is replaced by a heteroaryl group as defined above.

The term "pharmaceutically effective amount" refers to an amount effective in treating a virus infection, for example an HCV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HCV infection, in a patient. As used herein, the term "patient" refers to a mammal, including a human.

As used herein, the compounds of this technology are defined to include pharmaceutically acceptable derivatives or prodrugs thereof. A "pharmaceutically acceptable derivative or prodrug" includes a pharmaceutically acceptable salt, ester, salt of an ester, or other derivative of a compound of this technology which, upon administration to a recipient, is capable of providing (directly or indirectly) a compound of this technology. Particularly favored derivatives and prodrugs are those that increase the bioavailability of the compounds of this technology when such compounds are administered to a mammal (e.g., by allowing an orally administered compound to be more readily absorbed into the blood) or which enhance delivery of the parent compound to a biological compartment (e.g., the brain or lymphatic system) relative to the parent species. Examples of prodrugs of hydroxy containing compounds are amino acid esters or phosphonate or phosphate esters that can be cleaved in vivo hydrolytically or enzymatically to provide the parent compound. These have the advantage of providing potentially improved solubility.

The HCV inhibitors of the present technology should generally also retain inhibitory activity, or potency, over a broad spectrum of related but non-identical viruses. In particular, the HCV inhibitors of the present technology should inhibit all HCV virus strains that contain a gene sequence of the protease region that is typified by one or more 'wild type' strains derived from patients who are infected with HCV that contain mutations in the protease gene.

The compounds of this technology can contain one or more asymmetric carbon atoms and thus occur as racemates and racemic mixtures, single enantiomers, diastereomeric mixtures and individual diastereomers. All such isomeric forms of these compounds are expressly included in the technology. Each stereogenic carbon can be of the R or S configuration. Although the specific compounds exemplified in this application can be depicted in a particular stereochemical configuration, compounds having either the opposite stereochemistry at any given chiral center or mixtures thereof are also envisioned.

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorph or polymorph mixtures are included in the present application.

It is also to be understood that the compounds provided herein may have tautomeric forms. All such tautomeric forms are included within the scope of the instant disclosure. For example, a 3-enamino-2-oxindole where the amino group of the enamine has a hydrogen substituent has the tautomeric form of a 3-imino-2-hydroxyindole.

Pharmaceutical Compositions

The compounds of the present technology can be administered as their pharmaceutical compositions. The pharmaceutical compositions of the present technology comprise a therapeutically effective amount of a compound of the present technology formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are: sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants, according to the judgment of the formulator.

The compounds of the technology can be administered in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include salts with an inorganic base, organic base or basic or acidic amino acid. Inorganic bases which form pharmaceutically acceptable salts include alkali metals such as sodium or potassium, alkali earth metals such as calcium and magnesium, aluminum, and ammonia. Organic bases which form pharmaceutically acceptable salts include trimethylamine, triethylamine, pyridine, picoline, ethanolamine, diethanolamine, triethanolamine, dicyclohexylamine. Basic amino acids to form the salt include arginine, lysine and ornithine. Acidic amino acids to form the salt include aspartic acid and glutamic acid.

The pharmaceutical compositions of this technology can be administered to humans and other animals orally, rectally, parenterally, intracisternally, intravaginally, intraperitoneally, topically (as by powders, ointments, or drops), buccally, or as an oral or nasal spray. The term parenteral as used herein includes subcutaneous, intracutaneous, intravenous, intramuscular, intra-articular, intrasynovial, intrasternal, intrathecal, and intralesional injection or infusion techniques Liquid dosage forms for oral administration include pharmaceutically acceptable emulsions, microemulsions, solutions, suspensions, syrups and elixirs. In addition to the active compounds, the liquid dosage forms may contain inert diluents, commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitol, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to methods known in the art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form can be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers can include poly (orthoesters) and poly(anhydrides). Depot injectable formulations are also prepared by entrapping the drug in liposomes or microemulsions which are compatible with body tissues.

In some embodiments, the pharmaceutical compositions can include α-, β-, or γ-cyclodextrins or their derivatives. In certain embodiments, co-solvents such as alcohols can improve the solubility and/or the stability of the compounds in pharmaceutical compositions. In the preparation of aqueous compositions, addition salts of the compounds can be suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with $C_1$-$C_6$alkyl, such as methyl, ethyl or isopropyl, e.g. randomly methylated β-CD; hydroxy $C_{16}$ alkyl, particularly hydroxyethyl, hydroxypropyl or hydroxybutyl; carboxy $C_1$-$C_6$alkyl, particularly carboxymethyl or carboxyethyl; $C_1$-$C_6$alkyl -carbonyl, particularly acetyl; $C_1$-$C_6$ alkyloxycarbonyl$C_1$-$C_6$alkyl or carboxy$C_1$-$C_6$alkyloxy$C_1$-$C_6$alkyl, particularly carboxymethoxypropyl or carboxyethoxypropyl; and $C_1$-$C_6$alkylcarbonyloxy$C_1$-$C_6$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxy-propyl-γ-CD and (2-carboxymethoxy)propyl-β-CD, and in particular 2-hydroxypropyl-β-CD (2-HP-β-CD).

The term "mixed ether" denotes cyclodextrin derivatives where at least two cyclodextrin hydroxy groups are etherified with different groups such as, for example, hydroxypropyl and hydroxyethyl.

Compositions for rectal or vaginal administration can be suppositories which can be prepared by mixing the compounds of this technology with suitable non-irritating excipients or carriers such as cocoa butter, polyethylene glycol or a suppository wax, which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The pharmaceutical compositions can be formulated for nasal aerosol or inhalation and can be prepared as solutions in saline, and benzyl alcohol or other suitable preservatives, absorption promoters, fluorocarbons, or solubilizing or dispersing agents.

Dosage forms for topical or transdermal administration of a compound of this technology include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this technology. The ointments, pastes, creams and gels may contain, in addition to an active compound of this technology, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this technology, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It can further be convenient to formulate the compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds can also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration can depend on the condition of the subject, co-medication and the like.

Advantageously, the composition contains at least one additional compound having anti-HCV activity, where the additional compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. More advantageously, the additional other compound having anti-HCV activity is effective to inhibit the function of target in the HCV life cycle other than the HCV NS3 protease protein.

The additional compound having anti-HCV activity may be an interferon, such as interferon alpha 2B, pegylated interferon alpha, consensus interferon, interferon alpha 2A, or lymphoblastoid interferon tau. The compound having anti-HCV activity also can be interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, or rimantadine. Advantageously, the composition comprises An NS5 inhibitor as described above, together with an interferon and ribavirin.

The compound having anti-HCV activity may be a small molecule compound, advantageously a compound that is active when administered orally. A "small molecule compound" typically is a compound having a molecular weight up to about 1000 or 1500 daltons. Advantageously, the small molecule compound inhibits the function of at least one HCV target such as HCV metalloprotease, HCV serine protease, HCV polymerase, HCV helicase, HCV NS4B protein, HCV entry, HCV assembly, HCV egress, HCV NS5A protein, or inosine monophophate dehydrogenase ("IMPDH"). For example, the small molecule compound may be a nucleoside analog that inhibits HCV polymerase.

For example, HCV inhibitor compounds that can be formulated with and/or administered with the NS3 inhibitor compounds described above include those disclosed in WO 02/04425, WO 03/007945, WO 03/010141, WO 03/010142, WO 03/010143, WO 03/000254, WO 01/32153, WO 00/06529, WO 00/18231, WO 00/10573, WO 00/13708, WO 01/85172, WO 03/037893, WO 03/037894, WO 03/037895, WO 02/100851, WO 02/100846, EP 1256628, WO 99/01582, WO 00/09543.

Compounds that can be administered with the NS3 inhibitors described above, either by separate administration or combining the compounds into a composition include: Omega IFN (IFN-ω, BioMedicines Inc., Emeryville, Calif.); BILN-2061 (serine protease inhibitor, Boehringer Ingelheim Pharma KG, Ingelheim, Germany); Summetrel (antiviral, Endo Pharmaceuticals Holdings Inc., Chadds Ford, Pa.); Roferon A (IFN-α2a, F. Hoffmann-La Roche Ltd, Basel, Switzerland); Pegasys (PEGylated IFN-α2a (F. Hoffmann-La Roche Ltd); Pegasys and ribavirin (PEGylated IFN-α2a and ribavirin, F. Hoffmann-La Roche); CellCept (HCV IgG immunosuppressant, F. Hoffmann-La Roche); Wellferon (lymphoblastoid IFN-αn1 GlaxoSmithKline PLC, Uxbridge, UK); Albuferon-α (albumin IFN-α2b, Human Genome Sciences Inc., Rockville, Md.); Levovirin (ribavirin, ICN Pharmaceuticals, Costa Mesa, Calif.); IDN-6556 (caspase inhibitor, Idun Pharmaceuticals Inc., San Diego, Calif.); IP-501 antifibrotic Indevus Pharmaceuticals Inc., Lexington, Mass. Actimmune IFN-.gamma. InterMune Inc., Brisbane, Calif.); Infergen A IFN alfacon-1 InterMune Pharmaceuticals Inc., Brisbane, Calif.); ISIS 14803 (antisense, ISIS Pharmaceuticals Inc, Carlsbad, Calif./Elan Pharmaceuticals Inc., New York, N.Y.); JTK-003 (RdRp inhibitor, Japan Tobacco Inc., Tokyo, Japan); Pegasys and Ceplene (PEGylated IFN-α2a/immune modulator, Maxim Pharmaceuticals Inc., San Diego, Calif.); Ceplene (immune modulator, Maxim Pharmaceuticals Inc., San Diego, Calif.); Civacir (HCV IgG immunosuppressant, Nabi Biopharmaceuticals Inc., Boca Raton, Fla.); Intron A and Zadaxin (IFN-α2b/α1-thymosin, RegeneRx Biopharmiceuticals Inc., Bethesda, Md./SciClone Pharmaceuticals Inc, San Mateo, Calif.); Levovirin (IMPDH inhibitor, Ribapharm Inc., Costa Mesa, Calif.); Viramidine (IMPDH inhibitor Ribapharm Inc., Costa Mesa, Calif.); Heptazyme (ribozyme, SIRNA, Boulder, Colo.); Intron A (IFN-α2b, Schering-Plough Corporation, Kenilworth, N.J.); PEG-Intron (PEGylated IFN-α2b, Schering-Plough);Rebetron (IFN-α2b/ribavirin, Schering-Plough); PEG-Intron/ribavirin (PEGylated IFN-α2b/ribavirin, Schering-Plough); SCH-503034 (serine protease inhibitor, Schering-Plough); Zadazim (immune modulator, SciClone Pharmaceuticals Inc., San Mateo, Calif.); Rebif (IFN-β1a, EMD Serono, Geneva, Switzerland); IFN-β and EMZ701 (Transition Therapeutics Inc., Ontario, Canada); T67 (β-tubulin inhibitor, Amgen/Tularik Inc., South San Francisco, Calif.); VX-497 (IMPDH inhibitor Vertex Pharmaceuticals Inc., Cambridge, Mass.); VX-950/LY-570310 (serine protease inhibitors, Vertex/Eli Lilly and Co. Inc., Indianapolis, Ind.) Omniferon (natural IFN-α, Viragen Inc., Plantation, Fla.); XTL-002 (monoclonal antibody, XTL Biopharmaceuticals Ltd., Rehovot, Israel).

Methods of Treating HCV Infection

The compounds of the present invention are useful in the treatment of individuals infected by HCV and for the prophylaxis of these individuals. The present invention may be useful in the treatment of mammals infected with viruses whose existence is mediated by, or depends upon, the HCV protease enzyme. The inhibitors are administered in a pharmaceutically effective amount.

The compounds of the invention may be administered to an uninfected or HCV-infected patient either as a single agent or in combination therapy with other anti-viral agents to increase the therapeutic effect of these compounds. Thus, the present invention also relates to compositions comprising a compound of the present invention, and one or more compounds as a combined preparation for simultaneous, separate or sequential use in treatment of HCV infections. The combination may in some cases provide a synergistic effect, whereby viral infectivity and its associated symptoms may be substantially reduced or eliminated completely.

Dosage levels of between about 0.01 and about 1000 milligram per kilogram ("mg/kg") body weight per day, preferably between about 0.5 and about 250 mg/kg body weight per day of the NS3 inhibitor compounds as described above are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending upon the subject being treated and the particular mode of administration.

The skilled artisan will appreciate that lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. In some circumstances, an excalating dosage regime may be used where the dosage is increased by small increments until the optimum desired effect is obtained. In general, the preferred dosage is one that produces an effective antiviral result without causing any harmful or deleterious side effects, or where any unwanted effects are outweighed by the therapeutic benefit of the protease inhibitor.

When combinations of an NS3 inhibitor as described above and an additional anti-HCV agent are used, both the NS3 inhibitor and the additional agent usually are present at dosage levels of between about 10 to 100%, and advantageously between about 10 and 80% of the dosage normally administered in a monotherapy regimen.

When the NS3 inhibitors described above, or their pharmaceutically acceptable enantiomers, diastereomers, salts, solvates or prodrugs, are formulated together with a pharmaceutically acceptable carrier, the resulting composition may be administered in vivo to mammals, such as man, to inhibit HCV NS3 protease or to treat or prevent HCV virus infection. Advantageously, the method of administering the NS3 inhibitor is effective to inhibit the function of the HCV NS3 protease protein. In a preferred aspect, the method further comprises administering another compound having anti-HCV activity (as described above) prior to, after or concurrently with the NS3 inhibitor The NS3 inhibitors may also be used as laboratory reagents, for example in providing research tools for the design of viral replication assays, validation of animal assay systems and structural biology studies to gain insight into HCV disease mechanisms. The inhibitors also are useful in establishing or determining the binding site of other antiviral compounds, for example, by competitive inhibition. The inhibitors may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The NS3 inhibitors as described above, and compositions containing these inhibitors can be used for the manufacture of a medicament for treating HCV infection in a patient.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothionate) cytokines (e.g. Th2), modulators of cytokines, chemokines or the receptors thereof (e.g. CCR5) or hormones (e.g. growth hormone) to ameliorate, combat, or eliminate HCV infection and its symptoms.

Treating or preventing refers to alleviating or hindering symptoms or effects of an HCV viral infection in an infected animal, such as a mammal, particularly a human. Treating includes prophylaxis as well as the treatment of viral infections or symptoms of viral infections. The instant methods comprise treating an animal with a therapeutically effective amount of a compound or composition according to the instant invention. According to a preferred embodiment, the viral infection is an HCV infection.

Such combination therapy in different formulations may be administered simultaneously, separately or sequentially. Alternatively, such combinations may be administered as a single formulation, whereby the active ingredients are released from the formulation simultaneously or separately. Boosting The compounds of the present invention may also be administered in combination with compounds that modulate the metabolic degradation of the HCV inhibitors following application of the drug to an individual. These modulators include compounds that interfere with metabolic degradation by cytochrome enzymes, such as cytochrome P450. Suitable modulators are described in, for example, WO 2008/02234, the contents of which are hereby incorporated by reference in their entirety, although the skilled artisan will recognize that other modulators can be used. For example, other modulators that can be used include, but are not limited to: ritonavir, ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497.

The modulators may be administered simultaneously, separately or sequentially with the HCV inhibitors. Alternatively, the protease inhibitor and modulator can be combined into a single formulation, whereby the active ingredients are released from the formulation simultaneously or separately. The modulator is used in an amount that is effective at inhibiting degradation of the HCV protease inhibitor to an extent that permits achieving and maintaining a therapeutically effective blood and/or liver concentration of the inhibitor. It may be administered at the same or different ratio as the compound of the present invention. Preferably, the weight ratio of such modulator vs. a compound of the present invention (modulator:compound of the present invention) is 1:1 or lower, more preferably the ratio is 1:3 or lower, suitably the ratio is 1:10 or lower, more suitably the ratio is 1:30 or lower. The skilled artisan will recognize that the amount of the modulator that is to be used will vary with the nature of the modulator and of the HCV inhibitor, among other variables. Testing of HCV Protease Inhibitory Activity and Antiviral Activity The compounds of the invention may be tested in vitro for their ability to inhibit HCV protease and for their antiviral activity using methods that are well known in the art. For example, methods of testing the inhibition of HCV protease in vitro have been described, for example, by Taliani et al., *Anal. Biochem*, 240, 60-67 (1996). In these methods, apparent $IC_{50}$ values may be determined using a fluorogenic substrate. A suitable substrate is the peptide Ac-DE-D(Edans)-EE-Abu-ψ-[COO]-AS-K(Dabcyl)-NH2 (AnaSpec, San Jose, Calif., USA). This peptide contains two fluorophores in such proximity that their fluorescence is quenched. When the peptide is cleaved by HCV protease, the quenching is relieved, and an increase in fluorescence is observed.

Methods for testing the antiviral activity of the HCV protease inhibitors also are well known in the art. See, for example. U.S. Pat. No. 6,630,343. $IC_{50}$ values can be determined in a cell based, assay using the HCV Con1 subgenomic replicon. Cell lines containing Huh-luc/neo-ET with the persistent replicon sequence I389luc-ubi-neo/NS3-3'/ET can be obtained from ReBlikon GmbH [Schriesheim, Germany]. This construct expresses luciferase and the amount of luciferase protein is an accurate measure for RNA replication as determined by quantitative PCR (Taq-Man).

The specific compounds shown below and the following examples are illustrative of the compounds as described herein but are not to be construed as in any way, as limiting the scope of the claims set forth below.

EXAMPLES

The following experimental protocols are illustrative of the methods used to synthesize the HCV NS3 protease inhibitors of the technology. The skilled artisan will recognize that these exemplary methods are of general applicability.

Synthesis of Penicillamine Inhibitors

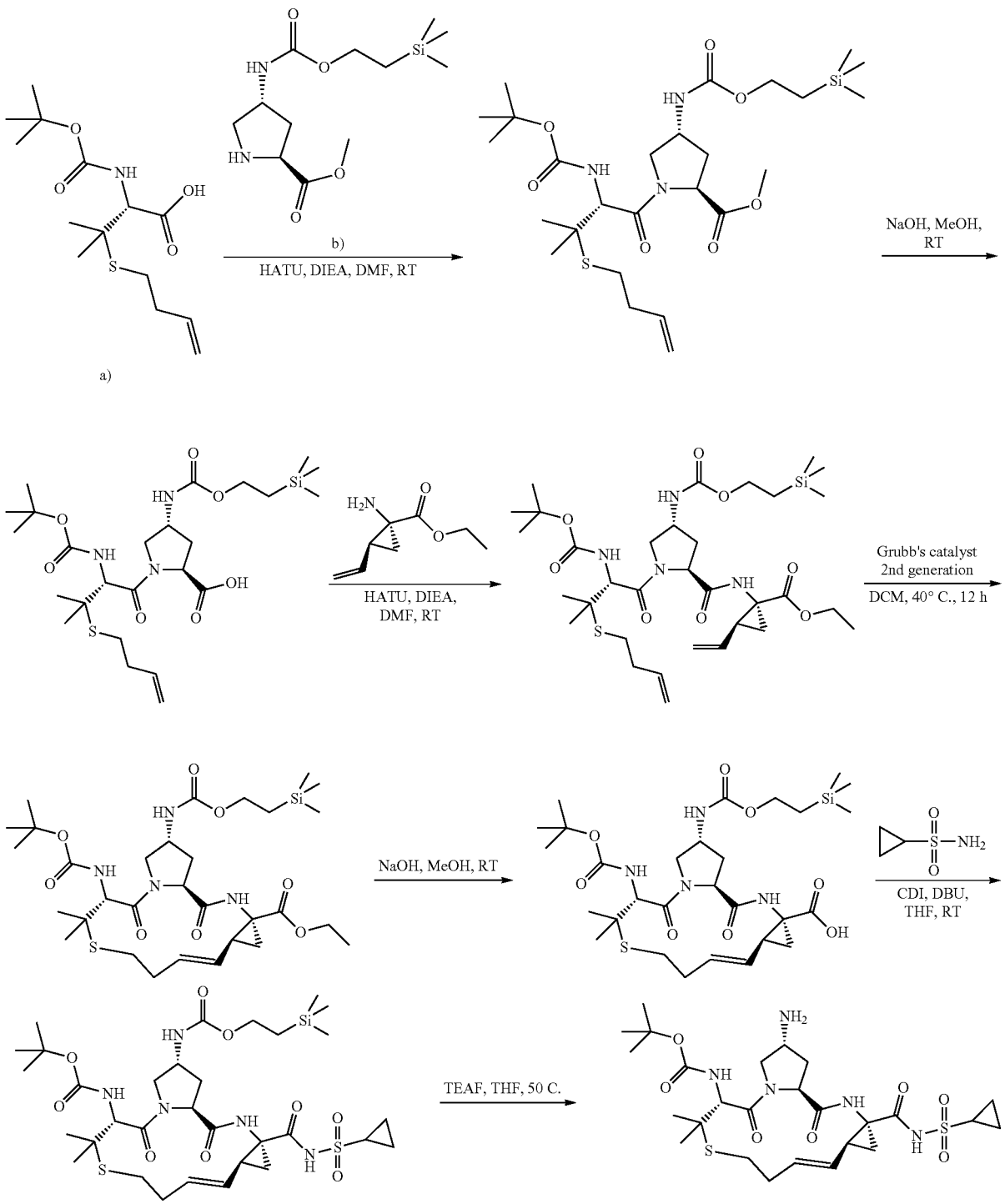

-continued
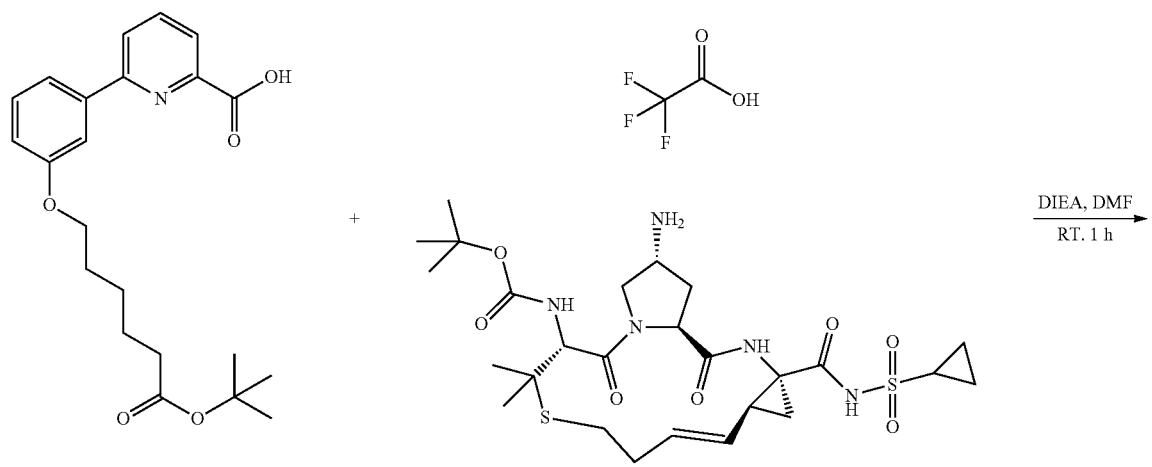
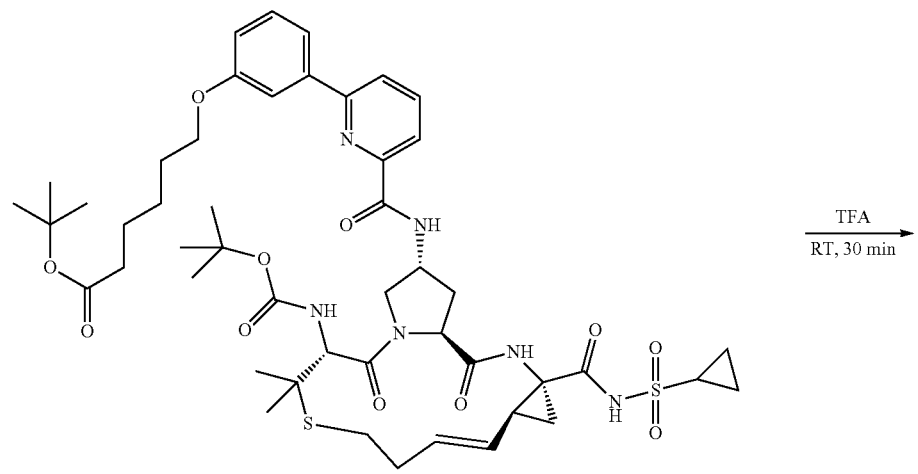
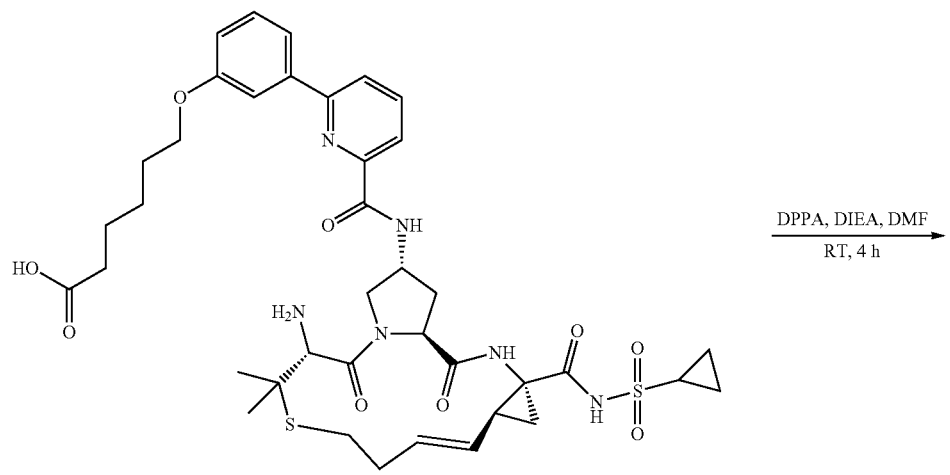

-continued
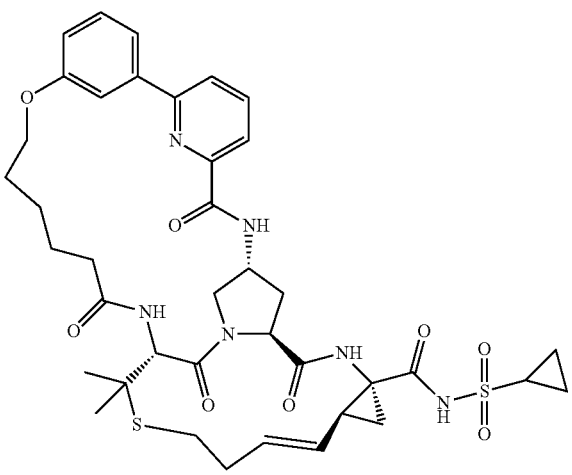
a) Tsantrizos, Y.S., *J. Organometal. Chem.* 691, 5163-5171, (2006). US2008/107623 A1
b) WO2005/37214
Synthesis of Common Precursor
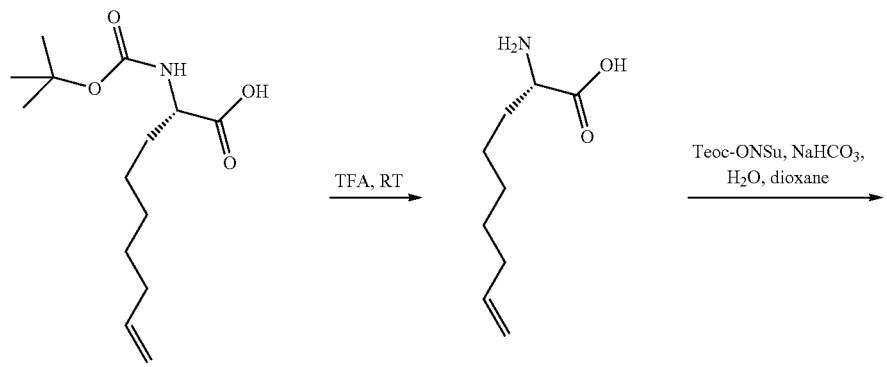
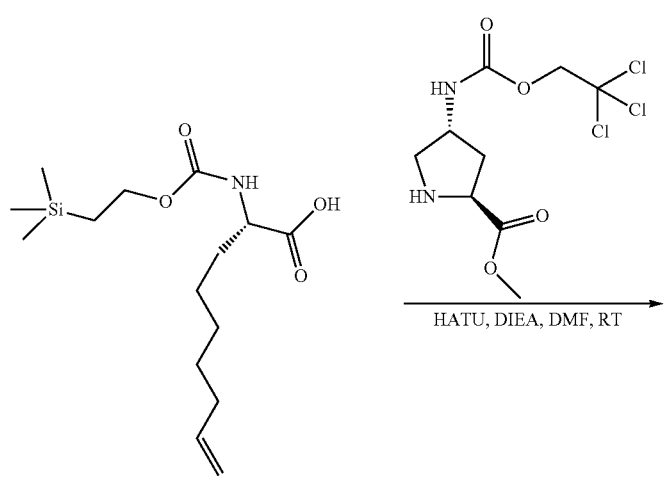

-continued
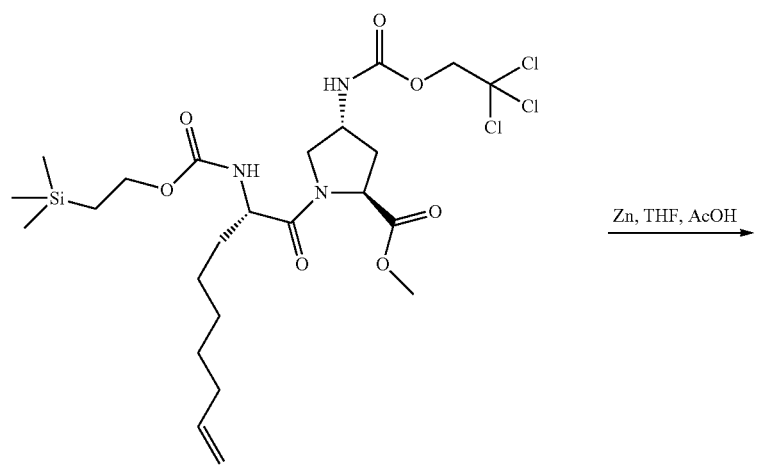
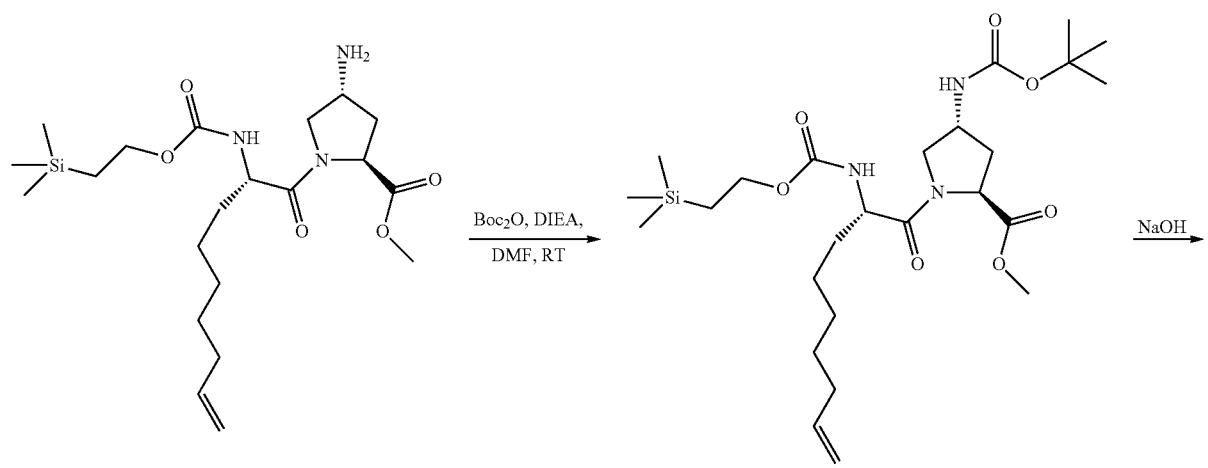
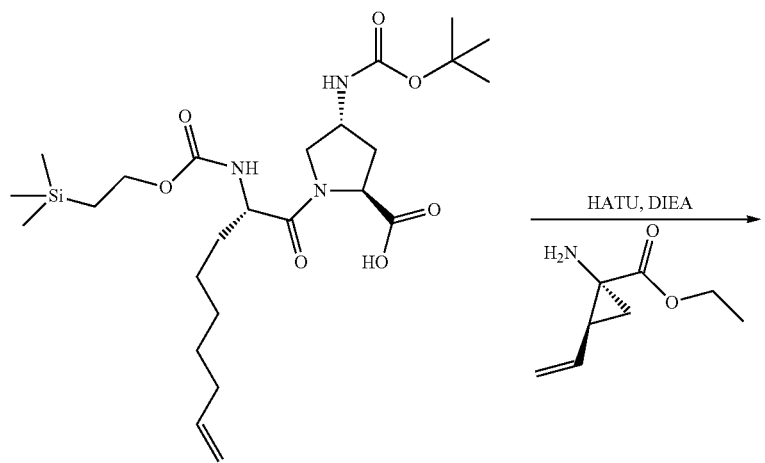

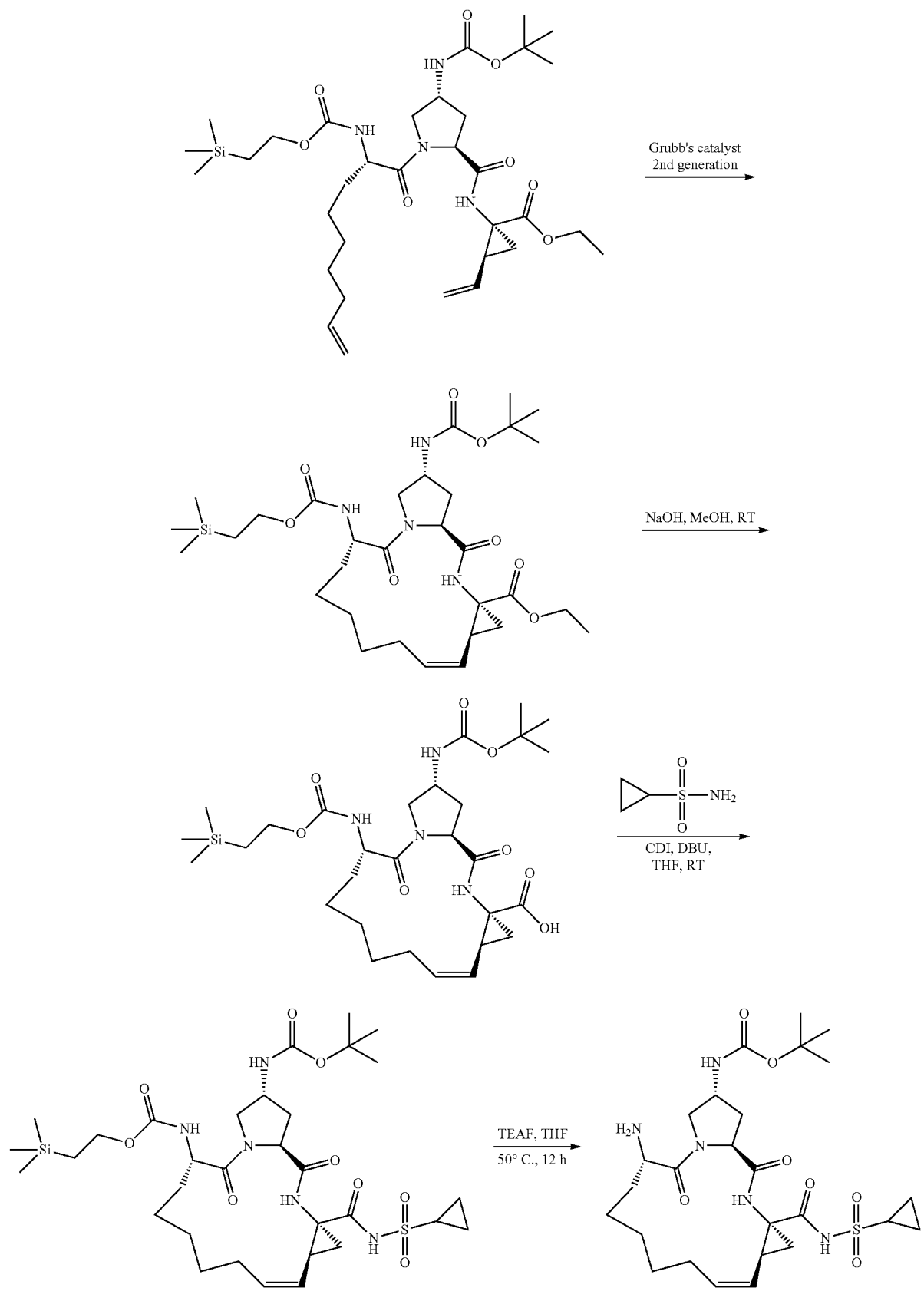

Synthesis of Protected Amino-proline

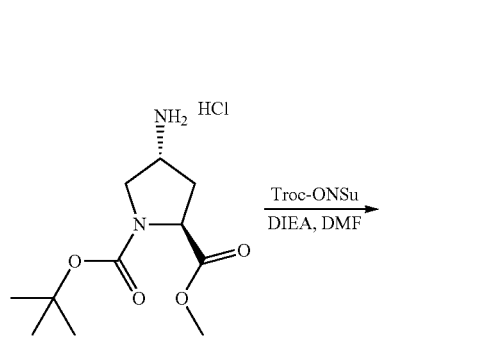

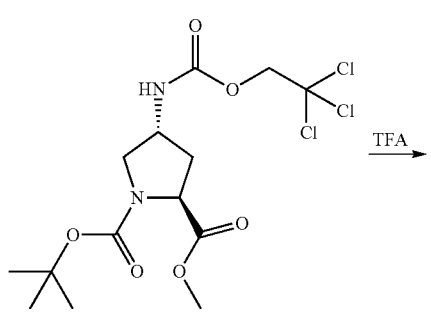

Synthesis of Compound I

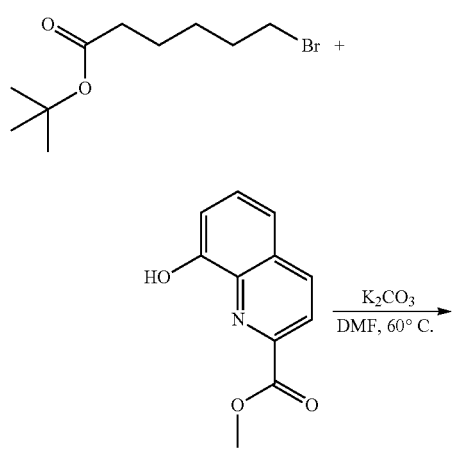

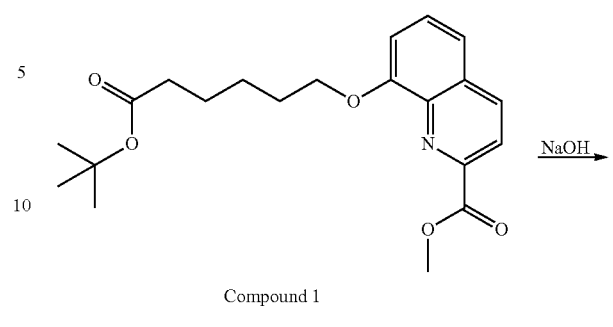

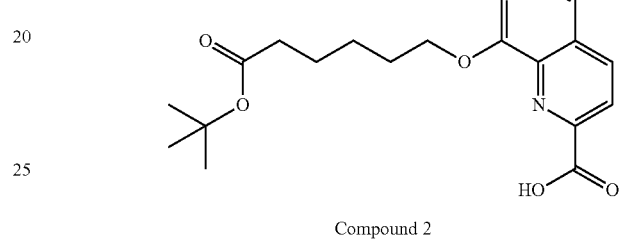

Methyl 8-(6-tert-butoxy-6-oxohexyloxy)quinoline-2-carboxylate (1)

To a solution of 8-hydroxyquinaldic acid methyl ester (406 mg, 2 mmol, 1 eq.) and t-butyl-6-bromohexanoate (754 mg, 3 mmol, 1.5 eq.) in DMF (5 mL) was added potassium carbonate (828 mg, 6 mmol, 3 eq.). The mixture was stirred vigorously for 3 h at 60° C., and then concentrated in vacuo. The residue was diluted with ethyl acetate, washed with $NaH_2PO_4$ buffer (pH 5, 1M) and brine, dried over $Na_2SO_4$ and concentrated in vacuo. Crude product was purified by flash chromatography on silica using ethyl acetate:hexanes gradient to provide 617 mg of 1. Yield 86%. MS m/z 374 $(M+H)^+$

8-(6-tert-butoxy-6-oxohexyloxy)quinoline-2-carboxylic acid (2)

To a solution of compound 1 (540 mg, 1.45 mmol, 1 eq.) in MeOH (3 mL) NaOH (116 mg, 2.9 mmol, 2 eq.) was added as, a concentrated aqueous solution, and the mixture was stirred at room temperature. The reaction was monitored by TLC (ethyl acetate/hexane/acetic acid, 1:1:0.01). Upon completion the volatiles were removed in vacuo and ethyl acetate added. The solution was washed with $NaH_2PO_4$ buffer (pH 5, 1M) and brine, dried over $Na_2SO_4$, and concentrated in vacuo to give 446 mg of crude 2, which was used directly in the next step. MS m/z 360 $[M-H]^+$

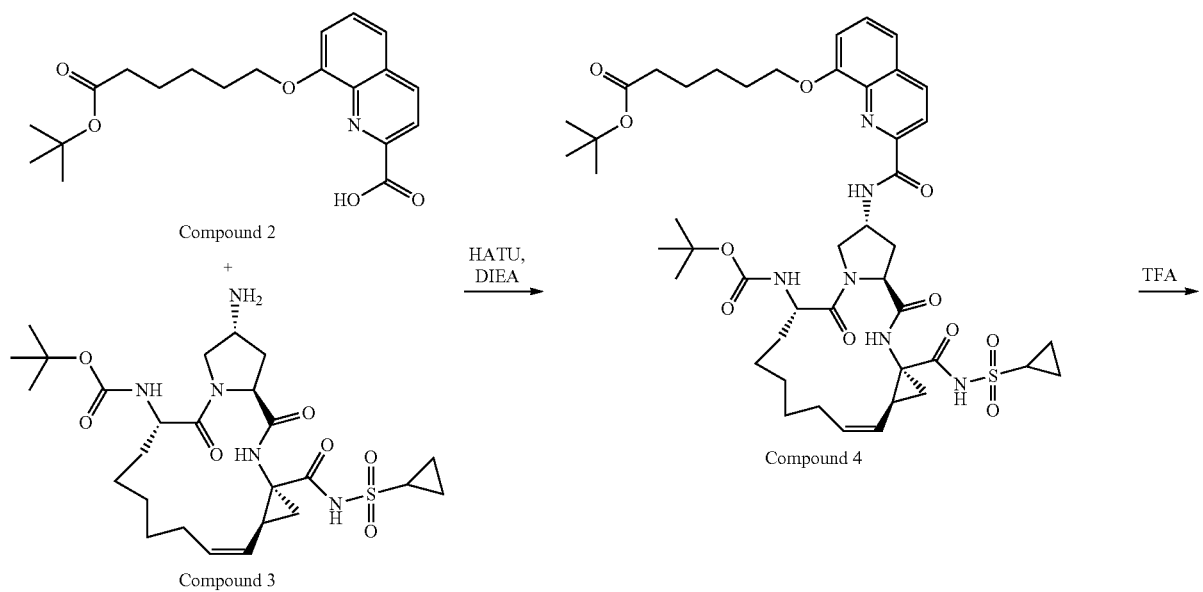

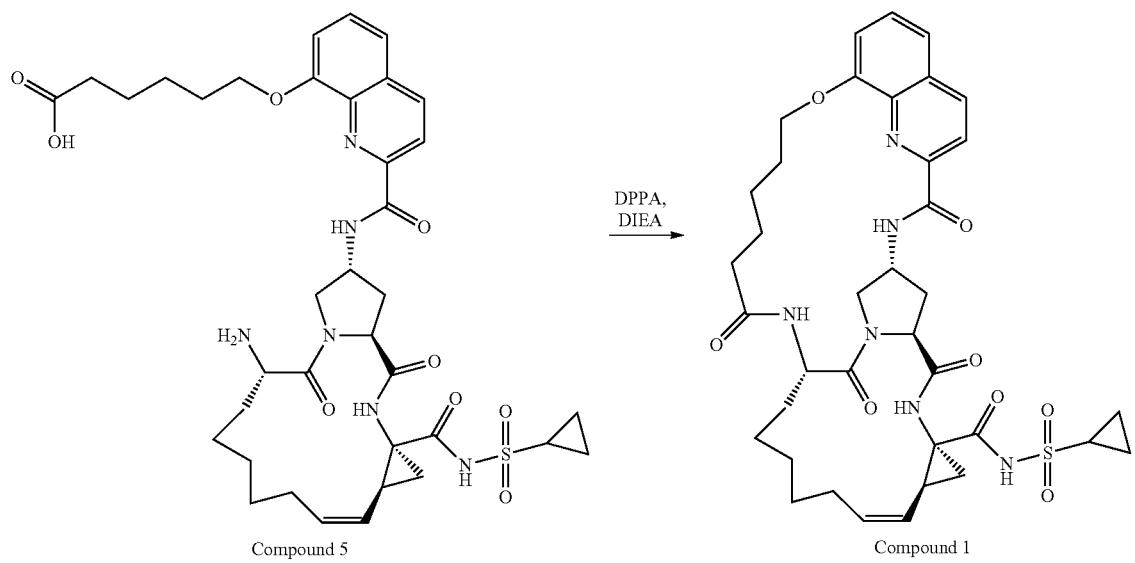

Compound 4

8-(6-tert-butoxy-6-oxohexyloxy)quinoline-2-carboxylic acid (2) (72 mg, 0.20 mmol) and HATU (92 mg, 0.24 mmol) were dissolved in 1 mL of dry DMF and DIEA (52 μL, 39 mg, 0.30 mmol) was added. The mixture was left to stand at RT for 30 min. Then the TFA salt of compound 3* (136 mg, 0.2 mmol) was added to the mixture, and the clear solution that formed was left to stand overnight at RT. Solvents were then evaporated in vacuo, and the residue was partitioned between ethyl acetate and 10% aq. $KHSO_4$. The organic phase was then washed with sat. aq. $NaHCO_3$ and brine, dried with anh. $MgSO_4$ and concentrated. The crude compound 4 was used for the next step without purification.

*Compound 3 was prepared according to WO 20054/095403

Compound 5

Compound 4 was dissolved in 2 mL of TFA and left to stand for 30 min. The volatiles were then removed an vacuo to provide the crude TFA salt of compound 5 which was used directly in the next step.

Compound I

Compound 5 from previous step was dissolved in DMF (15 mL) and the solution was made basic by addition of DIEA (0.4 mL). Then DPPA (432 μL, 550 mg, 2 mmol) and DIEA (344 μL, 258 mg, 2 mmol) were added and the mixture was left to stand overnight. Glacial acetic acid (200 μL) was then added followed after 30 min by conc. aqueous ammonia (300 μL). All volatiles were then removed an vacuo and the residue was dissolved in 4 mL of 50% aq. acetic acid. The product was then purified by RP-HPLC (column 2.1×25 cm, C18 Jupiter —Phenomenex, 10μ) using 0.1% TFA/acetonitrile gradient. The product containing fractions were collected, combine and lyophilized to give 70 mg of pure Compound I (48% over 3 steps). LC-MS m/z 733 (M−H)⁻.

Synthesis of COMPOUND VII

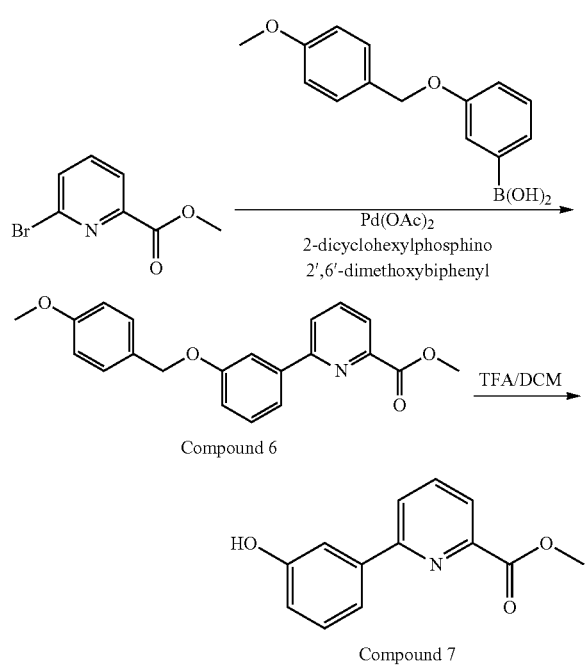

Compound 6

Compound 7

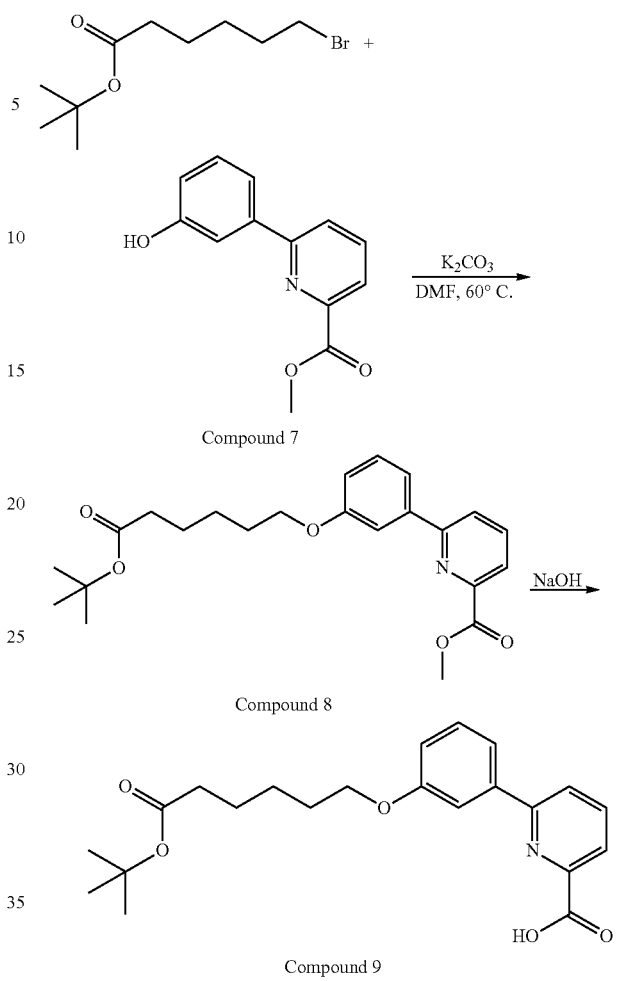

Compound 7

Compound 8

Compound 9

Methyl 6-[3-(4'-methoxybenzyloxy)]phenyl-2-carboxylate (6)

Methyl-6-bromopyridine-2-carboxylate (1.08 g, 5.00 mmol), 3-(4'-methoxy-benzyloxy)phenyl boronic acid (1.94 g, 7.50 mmol), K₃PO₄·H₂O (2.30 g, 10.00 mmol), 2-dicyclohexylphosphino-2'6'-dimethoxybiphenyl (0.20 g, 0.05 mmol) were combined in a 35 ml microwave vial and admixed with 15 ml of toluene and 1.5 ml of water. Subsequently, palladium acetate (45 mg, 0.20 mmol) was added and the vial was sealed with a Teflon cap and placed into a Discover microwave cavity. After irradiation at 180° C. for 20 min and subsequent gas jet cooling (down to 60° C.), the mixture was chromatographed using a silica gel MPLC column to give methyl 6-[3-(4'-methoxybenzyloxy)]phenyl-2-carboxylate (6) (1.48 g, 85%). MS 350.3 (M+H)⁺

Methyl 6-(3-hydroxy)phenyl-2-carboxylate (7)

To a solution of methyl 6-[3-(4'-methoxybenzyloxy)]phenyl-pyridine-2-carboxylate (6) (1.48 g, 4.24 mmol) in 20 ml of DCM at 0° C. under argon was added 20 ml TFA. The resulting solution was stirred at 0° C. for 2 hrs and then directly loaded onto a silica gel column and purified using 50% EtOAc in hexanes to give methyl 6-(3-hydroxy)phenyl-2-carboxylate (0.71 g, 73%). MS 230.0 (M+H)⁺

Methyl 6-(3-(6-tert-butoxy-6-oxohexyloxy)phenyl)picolinate (8)

To a solution of methyl 6-(3'-hydroxyphenyl)-pyridine-2-carboxylate (7) (600 mg, 2.6 mmol, 1 eq.) and t-butyl 6-bromohexanoate (980 mg, 3.9 mmol, 1.5 eq.) in DMF (7 mL) was added K₂CO₃ (1.08 g, 7.8 mmol, 3 eq.). The mixture was stirred vigorously overnight at 60° C. and then concentrated in vacuo. The residue was dissolved in ethyl acetate, washed with NaH₂PO₄ buffer (pH 5, 1M) and brine, dried over Na₂SO₄ and concentrated in vacuo. The crude product was purified by flash chromatography on silica using ethyl acetate:hexanes eluant to provide 730 mg of 8. Yield 73%. MS m/z 400 [M+H]⁺

6-(3-(6-tert-butoxy-6-oxohexyloxy)phenyl)picolinic acid (9)

To a solution of compound 8 (840 mg, 2.1 mmol, 1 eq.) in methanol (5 mL) was added NaOH (168 mg, 4.2 mmol, 2 eq.) dissolved in a minimum amount of water. The mixture was stirred at room temperature and monitored by TLC. After completion of the reaction volatiles were removed in vacuo and ethyl acetate added. The solution was washed with NaH₂PO₄ buffer (pH 5, 1M) and brine, dried over Na₂SO₄ and concentrated in vacuo to give 810 mg of crude compound 9, which was used directly in the next step. MS m/z 386 [M+H]⁺

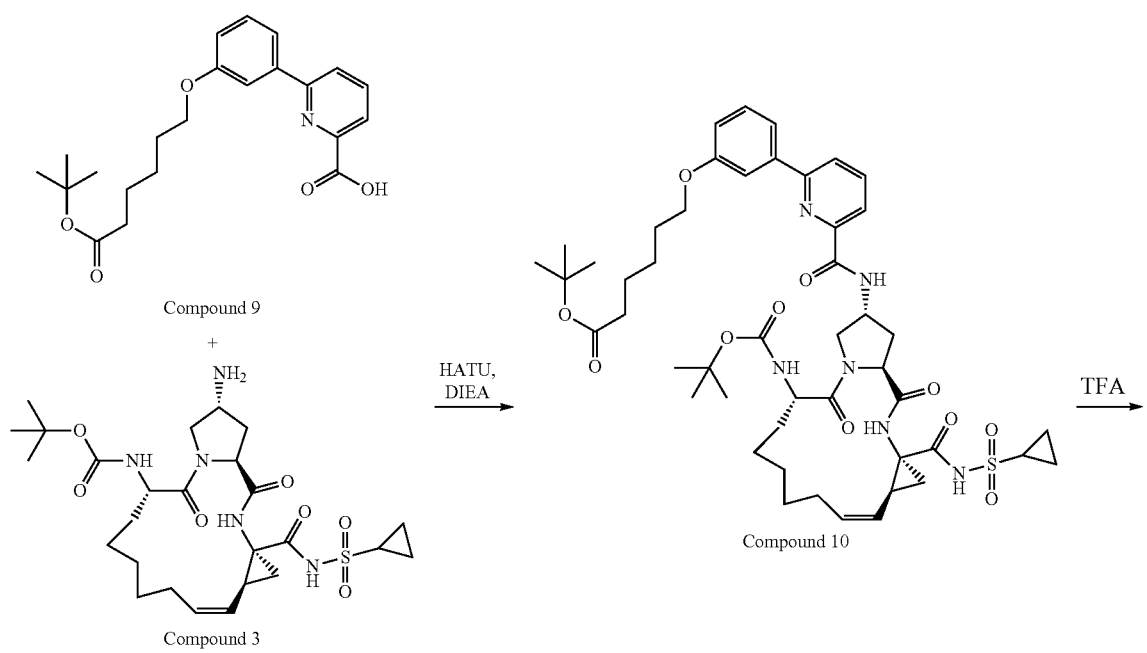

Compound 10

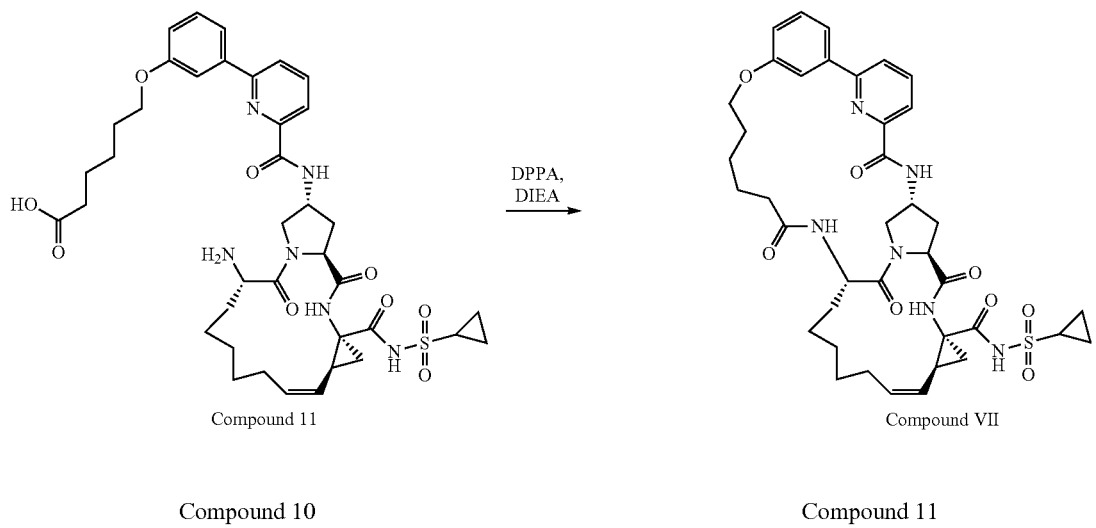

Compound 11

Compound 10

Compound 9 (38.5 mg, 0.1 mmol) and HATU (45.6 mg, 0.12 mmol) were dissolved in 0.5 mL of dry DMF and DIEA (26 μL, 19.5 mg, 0.15 mmol) was added. The mixture was left to stand at RT for 30 min. Then the TFA salt of compound 3 (68 mg. 0.1 mmol) was added to the mixture, and the clear solution thus formed was left to stand overnight at RT. Solvents were then evaporated in vacuo, and the residue was partitioned between ethyl acetate and 10% aq. $KHSO_4$. The organic phase was then washed with sat. aq. $NaHCO_3$ and brine, dried with anh. $MgSO_4$ and evaporated. The crude compound 10 was analyzed by HPLC and used for the next step without purification.

Compound 11

Compound 10 from the previous step was dissolved in 2 mL of TFA and left to stand for 30 min. The volatiles were then removed in vacuo and to provide the crude TFA salt of compound 11 that was used directly in the next step.

Compound VII

Compound 11 from the previous step was dissolved in DMF (10 mL) and the solution was made basic by addition of DIEA (0.2 mL). Then DPPA (216 μL, 275 mg, 1 mmol) and DIEA (172 μL, 129 mg. 1 mmol) were added and the mixture was left to stand overnight. Glacial acetic acid (200 μL) was then added followed after 30 min by conc. aqueous ammonia (300 μL). All volatiles were then removed in vacuo and the residue was dissolved in 3 mL of 50% aq. acetic acid. The product was then purified by RP-HPLC (column 2.1×25 cm. C18 Jupiter—Phenomenex, 10 μm) using 0.1% TFA/acetonitrile gradient. The product-containing fractions were lyophilized to give 34 mg of pure COMPOUND VII (45% of theory over 3 steps). Analysis by LC-MS gave one peak. MS m/z 759 (M–H Synthesis of Compound X

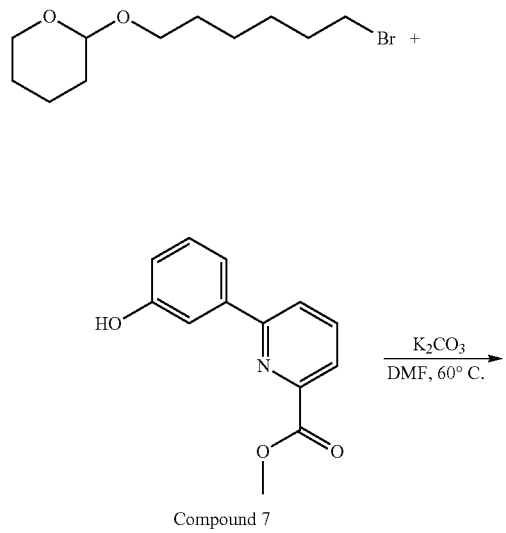

Compound 14

Methyl 6-(3-(6-(tetrahydro-2H-pyran-2-yloxy)hexyloxy)phenyl)picolinate (12)

To a solution of methyl 6-(3'-hydroxyphenyl)-pyridine-2-carboxylate (7) (250 mg, 1.1 mmol, 1.0 eq.) and 2-(6'-bromohexyloxy)tetrahydropyran (420 mg, 0.36 mL, 1.6 mmol, 1.5 eq.) in DMF (3 mL) was added K$_2$CO$_3$ (460 mg, 3.3 mmol, 3.0 eq.). The mixture was stirred vigorously overnight at 70° C. and then concentrated in vacuo. The residue was dissolved in ethyl acetate, washed with NaH$_2$PO$_4$ buffer (pH 5, 1M) and brine, dried over Na$_2$SO$_4$ and concentrated in vacuo. The crude product was purified by flash chromatography on silica using ethyl acetate:hexanes to provide 300 mg (65%) of 12. TLC R$_f$=0.5 (ethyl acetate:hexanes 1:1), MS m/z 330 (fragment after elimination of the THP group) [M+H]$^+$

Methyl 6-(3-(6-hydroxyhexyloxy)phenyl)picolinate (13)

To a solution of methyl 6-(3-(6-(tetrahydro-2H-pyran-2-yloxy)hexyloxy)phenyl) picolinate (12), (260 mg, 0.63 mmol) in methanol (1 mL) was added catalytic p-toluenesulfonic acid monohydrate (26 mg) and the mixture was stirred at RT for 2-4 h. The reaction was monitored by TLC (ethyl acetate:hexane 1:1). After completion the volatiles were removed in vacuo and the oily residue dissolved in ethyl acetate. The solution was washed with bicarbonate and brine, dried over sodium sulfate and concentrated in vacuo. The crude product was purified by gradient flash chromatography (ethyl acetate:hexane) to provide 135 mg (65%) of 13. TLC R$_f$=0.34 (ethyl acetate:hexanes 1:1), MS m/z 330 (M+H)$^+$

Methyl 6-(3-(6-(chlorocarbonyloxy)hexyloxy)phenyl)picolinate (14)

To a solution of methyl 6-(3-(6-hydroxyhexyloxy)phenyl) picolinate (13), (33 mg, 0.10 mmol, 1 eq.) in ethyl acetate (1 mL) was added triphosgene (14 mg, 0.047 mmol, 1.4 eq) dissolved in a minimum amount of ethyl acetate, followed immediately by DIEA (26 μL, 20 mg, 0.15 mmol, 1.5 eq). The mixture was stirred at room temperature for 30 min, the precipitated DIEA hydrochloride was filtered off, and the filtrate evaporated to dryness in vacuo. The oily residue of crude 14 was used directly for the next step.

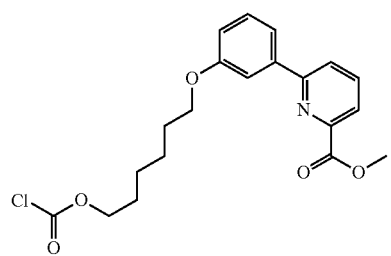

Compound 14

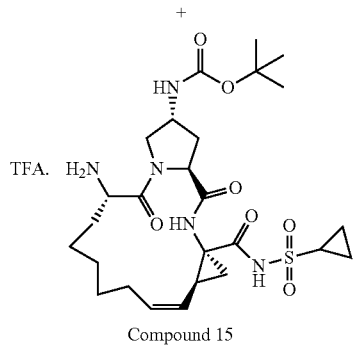

Compound 15

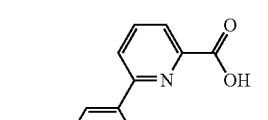

Compound 16

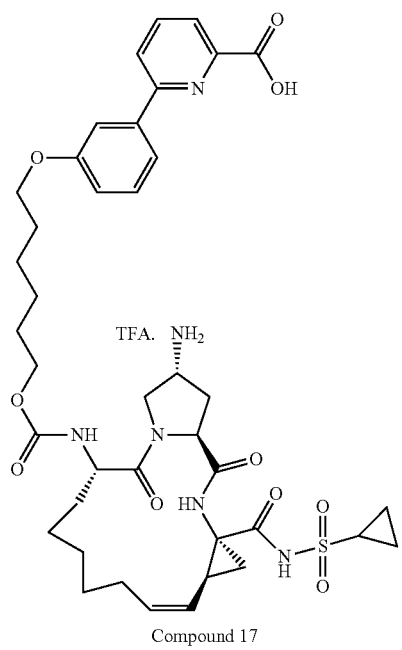

Compound 17

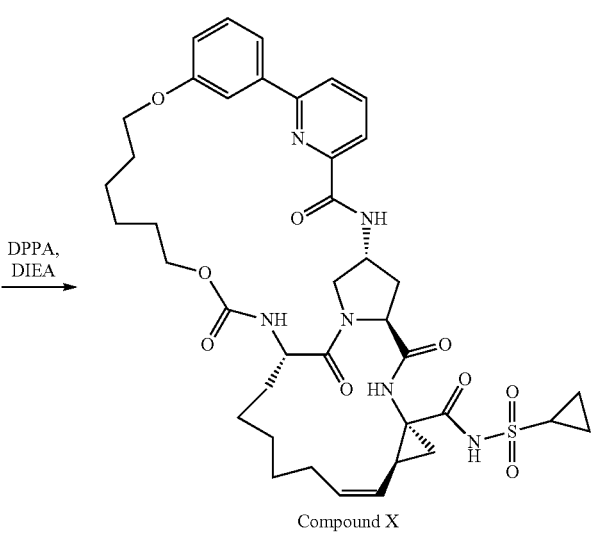

Compound X

Compound 16

Compound 15 (34 mg, 0.050 mmol) and DIEA (34 μL, 26 mg, 0.20 mmol) were dissolved in DMF (1 mL) and the solution was added to crude compound 14 from the previous step. The reaction mixture was left to stand 30 min at RT. Volatiles were then removed in vacuo and the oily residue dissolved in methanol (1 mL). NaOH (40 mg, 1.0 mmol) was dissolved in a minimal amount of water and added to the above solution. The reaction mixture was left to stand 30 min at RT and then evaporated to dryness. The residue was dissolved in 50% aqueous acetic acid (4 mL) and purified by RP-HPLC. The product-containing fractions were lyophilized to give 32 mg of pure compound 16 (70% over 2 steps). Analysis by LC-MS gave one peak. MS m/z 907 (M−H)−

Compound X

Compound 16 (32 mg, 0.035 mmol) was dissolved in 1 mL of neat TFA and the solution was left to stand 30 min at RT to provide the deprotected derivative (compound 3). The TFA was evaporated and the oily residue dissolved in DMF (10 mL). DIEA (172 µL, 129 mg, 1.0 mmol) and DPPA (108 µL, 137 mg, 0.50 mmol) were added and reaction mixture was stirred 3 hours at RT. Volatiles were then evaporated and the residue dissolved in 50% aqueous acetic acid (4 mL) and purified by RP-HPLC. The product-containing fractions were lyophilized to give 18 mg of pure COMPOUND X (46% over 3 steps). Analysis by LC-MS gave one peak. MS m/z 789 $(M-H)^-$

Synthesis of COMPOUND XVIII

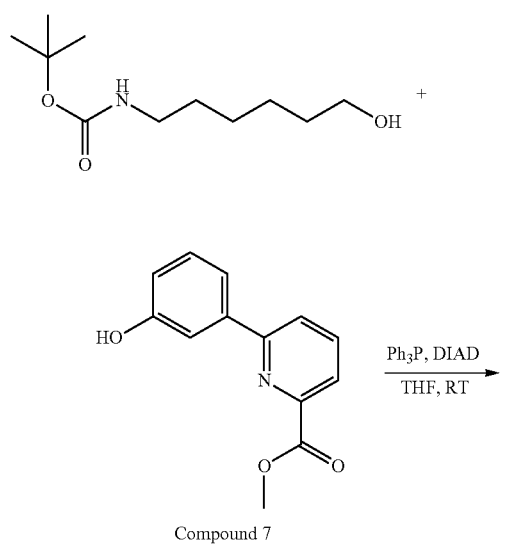

Compound 7

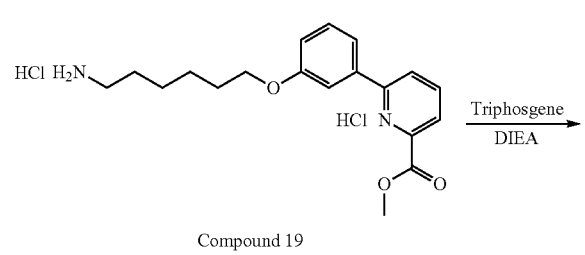

Compound 18

Compound 19

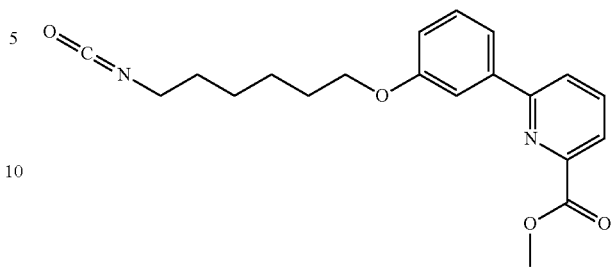

Compound 20

Methyl 6-(3-(6-(tert-butoxycarbonylamino)hexyloxy)phenyl)picolinate (18)

To a solution of methyl 6-(3'-hydroxyphenyl)-pyridine-2-carboxylate (7) (230 mg, 1.0 mmol, 1 eq.), tert-butyl 6-hydroxyhexylcarbamate (435 mg, 2.0 mmol, 2 eq.) and triphenylphosphine (525 mg, 2.0 mmol, 2 eq.) in anhydrous THF (3 mL), was added DIAD (0.39 mL, 2.0 mmol, 2 eq.) in THF (0.5 mL) dropwise. The reaction mixture was stirred at room temperature under argon for 2-4 h and monitored by TLC $R_f$=0.65 (ethyl acetate:hexanes 1:1). After completion of the reaction the volatiles were removed in vacuo. The crude 18 was purified by flash chromatography. MS m/z 429 $(M+H)^+$ Yield ~500 mg (>100%) product that contained ~20% of tert-butyl 6-hydroxyhexylcarbamate/DIAD adduct and was taken into the next step without further purification.

Methyl 6-(3-(6-aminohexyloxy)phenyl)picolinate dihydrochloride (19)

Methyl 6-(3-(6-(tert-butoxycarbonylamino)hexyloxy)phenyl)picolinate (18, all from the previous step, ~1 mmol) was dissolved in TFA (3 mL) and left to stand for 30 min. Volatiles were then evaporated, and the residue dissolved in 50% aq. acetic acid and purified by RP-HPLC. The product-containing fractions were lyophilized. The resulting oil was dissolved in 4M HCl in dioxane and evaporated (repeated 2x) to give 220 mg (55% over 2 steps) of 19 as a solid dihydrochloride. Analysis by LC-MS gave one peak. MS m/z 329 $(M+H)^+$

Methyl 6-(3-(6-isocyanatohexyloxy)phenyl)picolinate (20)

Methyl 6-(3-(6-aminohexyloxy)phenyl)picolinate dihydrochloride (19) (40 mg, 0.10 mmol) and DIEA (34 µL, 26 mg, 0.20 mmol) were dissolved in $CHCl_3$ (0.7 mL). Triphosgene (14 mg, 0.047 mmol) was dissolved in $CHCl_3$ (0.3 mL). The solutions were combined and a second portion of DIEA (34 µL, 26 mg, 0.20 mmol) was immediately added. The mixture was left to stand 30 min at RT and evaporated. The residue was dissolved in ethyl acetate and the precipitated DIEA hydrochloride was filtered off. The solvent was evaporated and the crude isocyanate (20) was used directly for the next step.

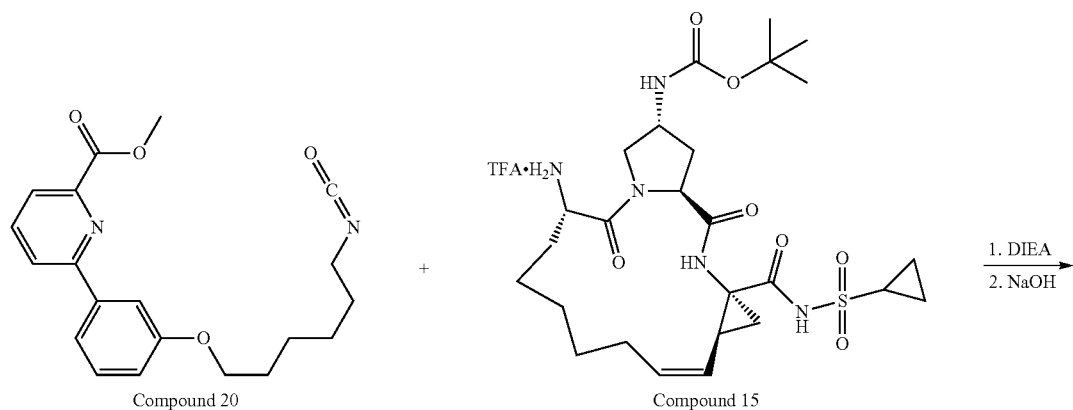
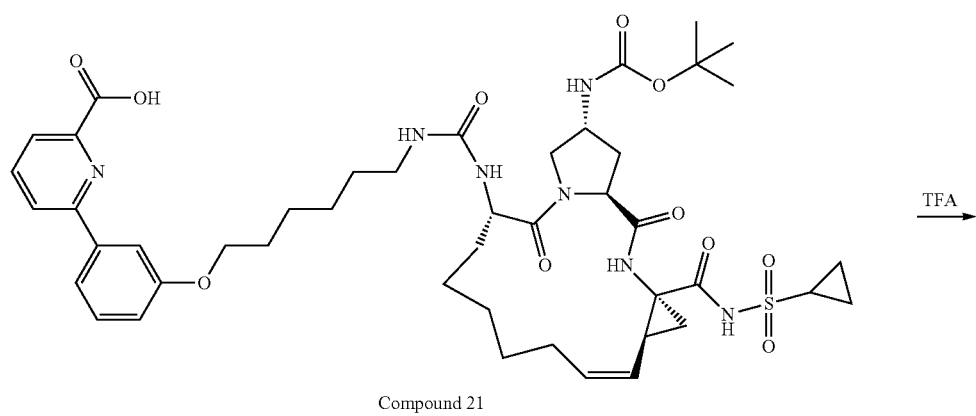
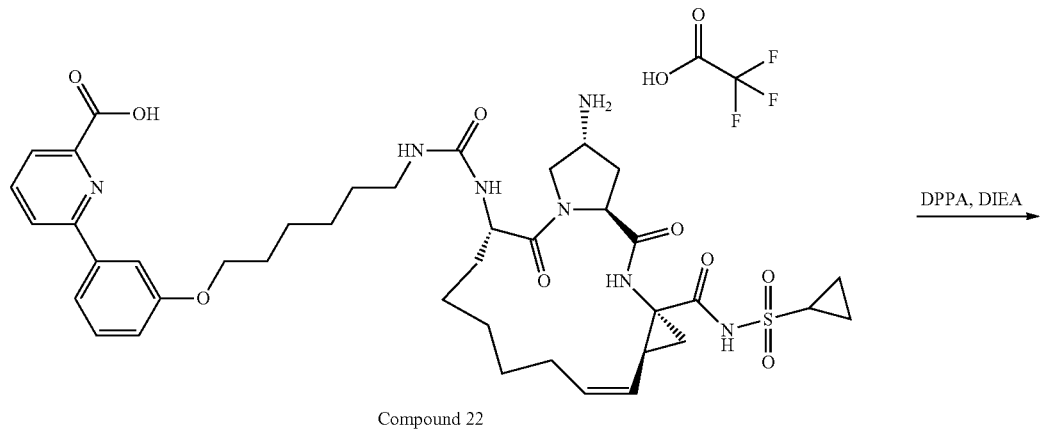

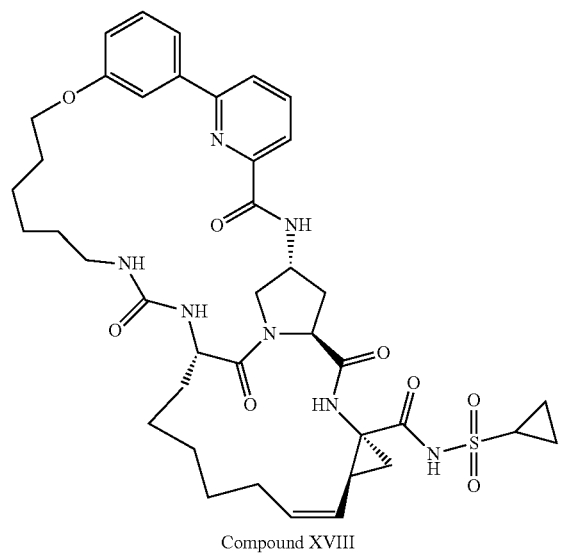 [SMILES: O=C1NCCCCCCOc2cccc(c2)-c2cccc(n2)C(=O)N[C@@H]2C[C@H]3C(=O)N[C@]4(C(=O)NS(=O)(=O)C5CC5)C[C@H]4/C=C\CCCCC[C@H](N1)C(=O)N3C2]

Compound XVIII

Compound 21

Compound 15 (34 mg, 0.050 mmol) and DIEA (34 μL, 26 mg, 0.20 mmol) were dissolved in DMF (1 mL) and the solution was added to the crude compound F from the previous step. The reaction mixture was left to stand 30 mm at RT. Volatiles were then removed in vacuo and the oily residue dissolved in methanol (1 mL). NaOH (40 mg, 1.0 mmol) was dissolved in a minimal, amount of water and added to the above solution. The reaction mixture was left to stand 30 min at RT and then evaporated to dryness. The residue was dissolved in 50% aqueous acetic acid (4 mL) and purified by RP-HPLC. The product-containing fractions were lyophilized to give 33 mg of pure compound 21 (72% over 2 steps). Analysis by LC-MS gave one peak. MS m/z 906 $(M-H)^-$

Compound XVIII

Compound 4 (33 mg, 0.036 mmol) from the previous step was dissolved in 1 mL of neat TFA and the solution was left to stand 30 min at RT to provide the deprotected derivative (compound 22). The TFA was evaporated and the oily residue dissolved in DMF (10 mL). DIEA (172 μL, 129 mg, 1.0 mmol) and DPPA (108 μL, 137 mg, 0.50 mmol) were added to this solution and the reaction mixture was stirred 3 hours at RT. Volatiles were then removed in vacuo and the residue dissolved in 50% aqueous acetic acid (4 mL) and purified by RP-HPLC. The product-containing fractions were lyophilized to give 17 mg of COMPOUND XVIII (46% over 3 steps). Analysis by LC-MS gave one peak. MS m/z 788 $(M-H)^-$

Synthesis of Compound XX

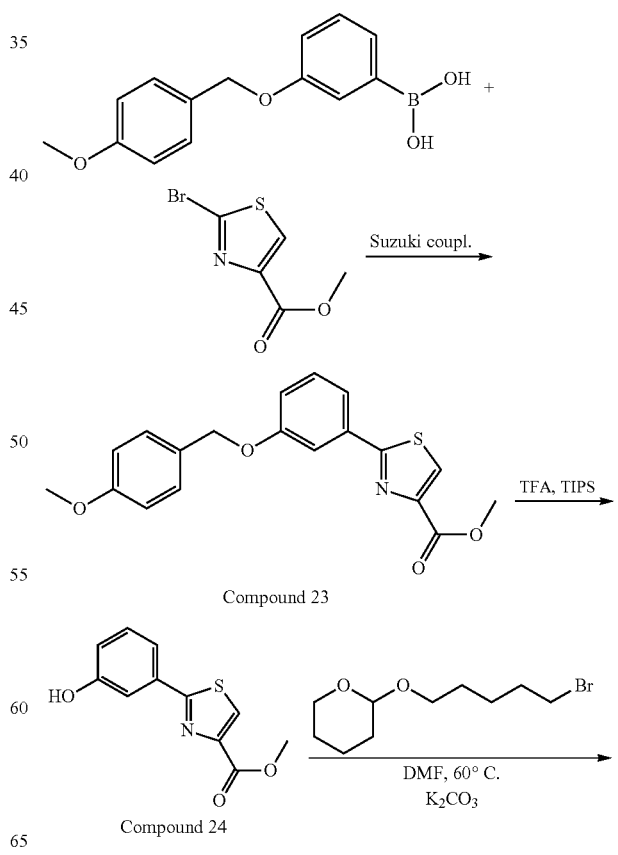

-continued

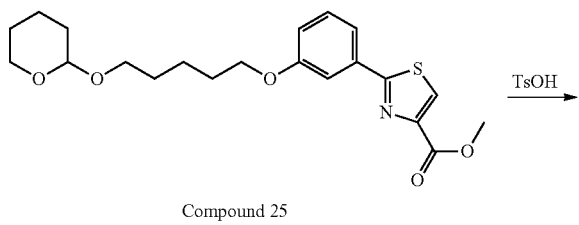

Compound 25

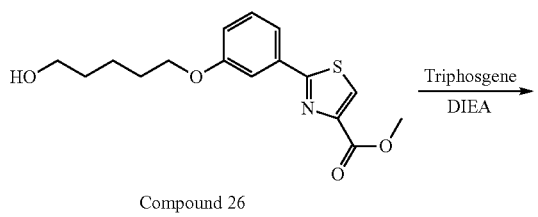

Compound 26

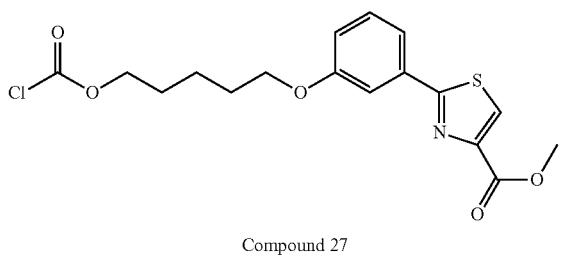

Compound 27

Methyl 2-(3-(4-methoxybenzyloxy)phenyl)thiazole-4-carboxylate (23)

3-(4-methoxybenzyloxy)phenylboronic acid (697 mg, 2.7 mmol, 1.5 eq.), methyl 2-bromothiazole-4-carboxylate (400 mg, 1.8 mmol, 1.0 eq.), dicyclohexyl (2',6'-dimethoxybiphenyl-2-yl) phosphine (74 mg, 0.18 mmol, 10 mol %) and $PdCl_2$ (20 mg, 0.090 mmol, 5 mol %) were dissolved in toluene (6 mL) and added to a solution of $K_3PO_4$ (828 mg, 3.6 mmol, 2.0 eq.) in water (0.6 mL). The reaction mixture was heated 20 min at 180° C. in a microwave reactor, allowed to cool, diluted with ethyl acetate, washed with brine, dried over anhydrous sodium sulfate and concentrated in vacuo. The crude 23 was used in the next step without purification.

Methyl 2-(3-hydroxyphenyl)thiazole-4-carboxylate (24)

The crude 23 from the previous step (~1.8 mmol) was dissolved in DCM (3 mL). TFA (3 mL) and TIPS chloride (410 uL, 2 mmol, 1.1 eq) were added and the solution stirred 20 min at RT. The volatiles were removed in vacuo. The crude product was purified by flash chromatography. Overall yield 400 mg (95%) of 24, MS m/z 236 (M+H)$^+$

Methyl 2-(3-(5-(tetrahydro-2H-pyran-2-yloxy)pentyloxy)phenyl)thiazole-4-carboxylate (25)

To a solution of methyl 2-(3-hydroxyphenyl)thiazole-4-carboxylate (24), (223 mg, 0.95 mmol, 1 eq.) and 2-(5-bromopentyloxy)tetrahydro-2H-pyran (357 mg, 1.42 mmol, 1.5 eq) in DMF (3 mL) was added powdered potassium carbonate (392 mg, 2.84 mmol, 3.0 eq.) The mixture was stirred vigorously for 4 h at 70° C., then concentrated in vacuo. The residue was diluted with ethyl acetate, washed with $NaH_2PO_4$ buffer (pH 5, 1M) and brine, dried over anhydrous sodium sulfate and concentrated in vacuo. The crude product was purified by flash chromatography (ethyl acetate:hexanes gradient). Yield 250 mg (65%). TLC $R_f$=0.44 (ethyl acetate: hexanes 3:7), MS m/z 322 (M+H)$^+$

Methyl 2-(3-(5-hydroxypentyloxy)phenyl)thiazole-4-carboxylate (26)

To a solution of methyl 2-(3-(5-(tetrahydro-2H-pyran-2-yloxy)pentyloxyphenyl)thiazole-4-carboxylate (25), (166 mg, 0.40 mmol, 1.0 eq.) in MeOH (0.7 mL) was added p-toluenesulfonic acid monohydrate (17 mg, 10 mol %) and the solution was stirred 4 h at RT. After completion of the reaction the volatiles were removed in vacuo and ethyl acetate added. The resulting solution was washed with saturated aqueous sodium bicarbonate, brine, dried over anhydrous sodium sulfate, and concentrated in vacuo. The crude 26 was used in the next step without purification. MS m/z 322 (M+H)$^+$

Methyl 2-(3-(5-(chlorocarbonyloxy)pentyloxy)phenyl)thiazole-4-carboxylate (27)

To a solution of methyl 2-(3-(5-hydroxypentyloxy)phenyl)thiazole-4-carboxylate (26), (32 mg, 0.10 mmol, 1.0 eq.) in ethyl acetate (1 mL) was added triphosgene (14 mg, 0.047 mmol, 1.4 eq) dissolved in a minimum amount of ethyl acetate, followed immediately by DIEA (26 μL, 20 mg, 0.15 mmol, 1.5 eq). The mixture was stirred at room temperature for 30 min, the precipitated DIEA hydrochloride was filtered off, and the filtrate evaporated to dryness in vacuo. The oily residue of crude compound 27 was used directly for the next step.

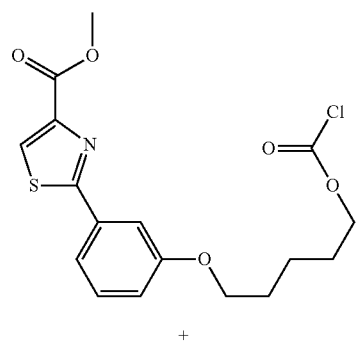

+  →

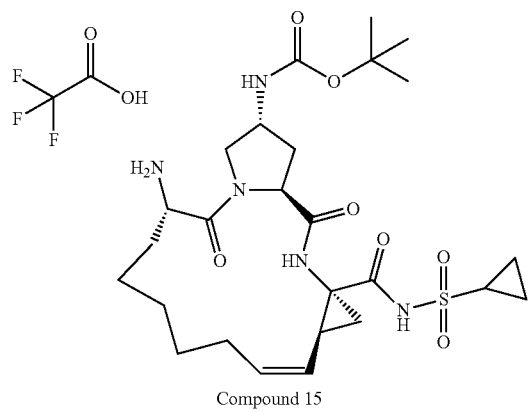
Compound 15
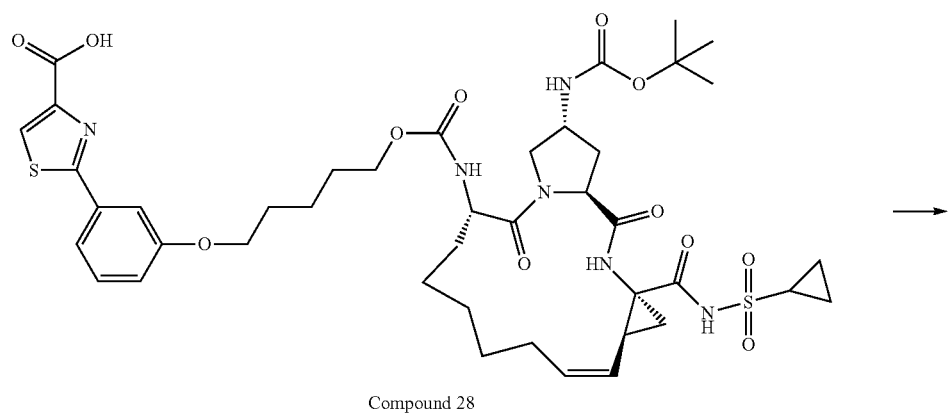
Compound 28
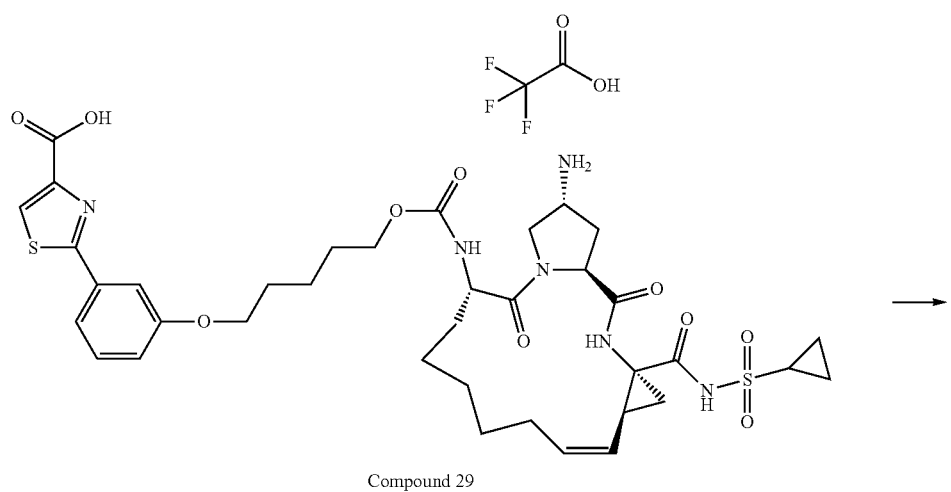
Compound 29

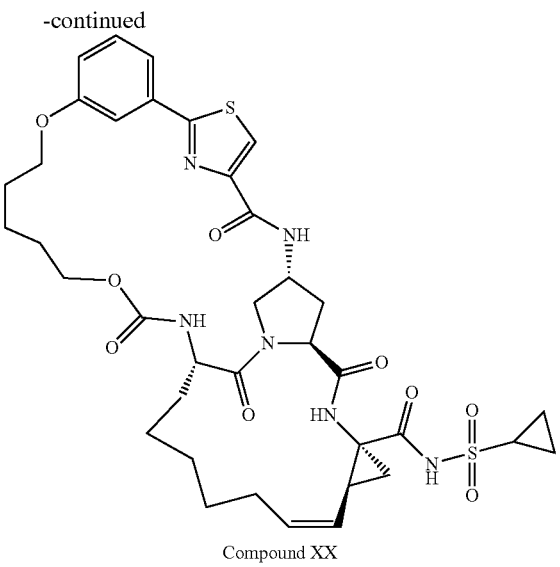

Compound XX

Compound 28

Compound 15 (34 mg, 0.050 mmol) and DIEA (34 μL, 26 mg, 0.20 mmol) were dissolved in DMF (1 mL) and the solution was added to the crude compound 27 from the previous step. The reaction mixture was left to stand 30 min at RT. Volatiles were then removed in vacuo and the oily residue dissolved in methanol (1 mL). NaOH (40 mg, 1.0 mmol) was dissolved in a minimal amount of water and added to the above solution. The reaction mixture was left to stand 30 min at RT and then evaporated to dryness. The residue was dissolved in 50% aqueous acetic acid (4 mL) and purified by RP-HPLC. The product-containing fractions were lyophilized to give 33 mg of pure compound 28 (73% over 2 steps). Analysis by LC-MS gave one peak. MS m/z 899 $(M–H)^-$

Compound XX

Compound 28 (32 mg, 0.035 mmol) was dissolved in 1 mL of neat TFA and the solution was left to stand 30 min at RT to provide the deprotected derivative 29. The TFA was evaporated and the oily residue dissolved in DMF (10 mL). DIEA (172 μL, 129 mg, 1 mmol) and DPPA (108 μL, 137 mg, 0.50 mmol) were added to this solution and the reaction mixture was stirred 3 hours at RT. Volatiles were then evaporated and the residue dissolved in 50% aqueous acetic acid (4 mL) and purified by RP-HPLC. The product-containing fractions were lyophilized to give 17 mg of COMPOUND XX (43% over 3 steps). Analysis by LC-MS gave one peak. MS m/z 781 $(M–H)^-$ List of Abbreviations
  THF Tetrahydrofuran
  THP 2-tetrahydropyranyl
  TEAF Tetraethylamonium fluoride
  Troc Trichloroethoxycarbonyl
  Teoc 2-Trimethylsilylethyloxycarbonyl
  CDI Carbonyldiimidazole
  ONSu O-succinimidyl ester
  TBTU O-benzotriazole-1-yl-N,N,N',N'-tetramethyluronium tetrafluoroborate
  RT Room temperature
  Pd/C Palladium on carbon
  HCl Hydrochloric acid
  MeOH Methanol
  $CH_3CN$ acetonitrile
  DBU 1,4-Diazabicyclo[5.4.0]undec-7-ene
  DCE Dichloroethane
  DMF Dimethylformamide
  $Et_3N$ triethylamine
  EtOAc Ethyl acetate
  DCM Dichloromethane
  DIPEA Diisopropylethylamine
  Boc tert-Butoxycarbonyl
  LHMDS Lithium Bis(trimethylsilyl)amide
  TIPS Triisopropylsilyl
  Fmoc-OSu 9-fluorenylmethoxycarbonyl N-hydroxysuccinimide ester
  DCE Dichloroethane
  NaOH Sodium hydroxide
  $MgSO_4$ Magnesium Sulfate
  $NaCNBH_3$ Sodium cyanoborohydride
  DMAP Dimethylaminopyridine
  Fmoc-OSu N-(9-Fluorenylmethoxycarbonyloxy) succinimide
  PG Protecting group
  LHMDS Lithium bis(trimethylsilyl)amide
  KOBu-t Potassium tert-butoxide
  HATU 2-(7-Aza-1H-benzotriazole-1-yl)-1,1,3,3-tetramethyluronium hexafluorophosphate;
  DIEA Diisopropylethyl amine;
  TFA Trifluoroacetic acid
  DPPA Diphenylphosphoryl azide
  RP-HPLC Reverse Phase High Performance Chromatography
  LC-MS Liquid Chromatography-Mass Spectrometry.

Purification and Analytical Procedures

Compounds requiring HPLC purification were purified on a system using a Gilson UV/VIS 156 detector, a Gilson 205 fraction collector, and a Gilson 321 pump.

Mobile phases used were as follows,

A: 0.1% TFA in water; B: acetonitrile

The column used was a Phenomenex 10 um C18, 300A, 250×21.2 mm

RP-HPLC separations were performed on a (C18 Jupiter—Phenomenex column (2.1×25 cm, 10 μm) using 0.1% TFA/acetonitrile gradient or 0.1% TFA/methanol.

Analytical LC-MS

LC-MS were run on an Agilent 1100 MSD in positive and negative modes using an ESI (Electrospray Ionization) source. Scan range is 100-2000 amu. Mobile phase used was A: 1% acetic acid in water and B: 1% acetic acid in acetonitrile. UV detection at 220 or 254 was used. The column most commonly used was ZORBAX 3.5 um, SB-C18, 2.1×30 mm. Mass (MS) calculations were made using the monoisotopic mass for the compound.

Prep-TLC: partisil PK6F, silica gel 60A with fluorescent indicator 1000 or 500 um from Whatman.

Flash Chromatography silica gel type: Silica gel 60, particle size 0.040~0.063 mm from EMD.

Microwave reactor CEM Discover NP-1008

Any reference to any of the instant compounds also includes a reference to pharmaceutically acceptable salts thereof.

Any reference to any of the instant compounds also includes a reference to a stereoisomer thereof.

Other substitutions, modifications, changes and omissions may be made in the design, operating conditions and arrangement of the exemplified embodiments without departing from the spirit of the technology as expressed in the appended claims.

Additional advantages, features and modifications will readily occur to those skilled in the art. Therefore, the technology in its broader aspects is not limited to the specific details, and representative compounds, compositions or methods shown and described herein. Accordingly, various modifications may be made without departing from the spirit or scope of the general inventive concept as defined by the appended claims and their equivalents.

The claims below are not restricted to the particular embodiments described above.

What is claimed is:

1. A compound represented by the formula:

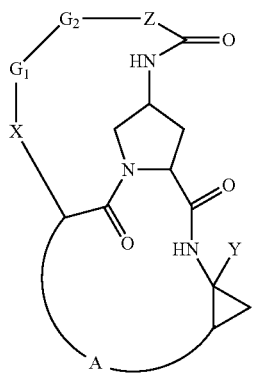

wherein,

Z is O, NH, or $(CH_2)_n$, wherein when Z is $(CH_2)_n$ then up to three methylene units of Z are optionally and independently replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NR-CONR—, —S—, —SO—, —SO$_2$—, —NR—, —SO$_2$NR—, or —NRSO$_2$NR— and wherein up to 3 carbon atoms of Z are optionally and independently mono- or disubstituted by R1;

X is —NHSO$_2$X$^1$— or

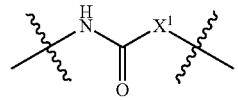

wherein $X^1$ is NH, O, or $(CH_2)_m$, wherein when $X^1$ is $(CH_2)_m$ then up to three methylene units of $X^1$ are optionally and independently replaced by alkenylene, alkynylene, $C_3$-$C_7$ cycloalkylene, $C_4$-$C_7$ cycloalkenylene, heterocycloalkylene, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—, and wherein up to 3 carbon atoms of $X^1$ are optionally and independently mono- or disubstituted by R1;

A is optionally substituted $C_4$-$C_{10}$ alkylene, wherein up to three methylene units of A are optionally and independently replaced by alkenylene, alkynylene, $C_3$-$C_7$ cycloalkylene, $C_4$-$C_7$ cycloalkenylene, heterocycloalkylene, heteroaryl, —CO—, —C(S)—, —CONR—, —COO—, —COOR—, —NRCO—, —O—, —NRCONR—, —S—, —SO—, —SO$_2$—, —NR—, —SO$_2$NR—, or —NRSO$_2$NR—, wherein up to 3 carbon atoms of A are optionally and independently mono- or disubstituted by R1;

Y is COOH, COOR, CONHR, —COCONHR, CONHSO$_2$R, CONH(SO$_2$)NRR, CONHP(O)(OR)$_2$, or CONHP(O)(OR)(NRR);

G1 and G2 independently are absent or are selected from the group consisting of monocyclic or bicyclic aryl or heteroaryl, optionally substituted by up to 3 R2 moieties, provided that at least one of G1 and G2 is present;

R is H, $C_1$-$C_6$ alkyl or $C_3$-$C_6$ cycloalkyl;

R1 is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, optionally substituted aralkyl, optionally substituted cycloalkyl, optionally substituted cycloalkenyl, optionally substituted heterocyclo, optionally substituted heteroaryl, amido, carboxyl, sulfonamido, halo, —OR, —CN, —NO$_2$, —NRR, or —OCF$_3$, R2 independently is selected from the group consisting of $C_1$-$C_{12}$ alkyl, $C_2$-$C_{12}$ alkenyl, $C_2$-$C_{12}$ alkynyl, $C_3$-$C_8$ cycloalkyl, $C_4$-$C_8$ cycloalkenyl, aryl, heteroaryl, and heterocyclo, each optionally substituted by up to three substitutents independently selected from the group consisting of optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_8$ cycloalkyl, optionally substituted $C_4$-$C_8$ cycloalkenyl, optionally substituted aryl, optionally substituted heteroaryl, optionally substituted heterocyclo, halo, —OR, —CN, —NO$_2$, —NRR, —OCF$_3$, —COOR, CONRR, COR, SO$_2$R, and SOR;

m is 0-9 and n is 0-9.

2. The compound according to claim 1 wherein G1 and G2 both are present.

3. The compound according to claim 1, wherein $X^1$ is $(CH_2)_m$ and wherein up to 3 carbon atoms of $X^1$ are optionally and independently mono- or disubstituted by optionally substituted $C_1$-$C_{12}$ alkyl.

4. The compound according to claim 1, wherein Z is $(CH_2)_n$ and wherein up to 3 carbon atoms of Z are optionally and independently mono- or disubstituted by optionally substituted $C_1$-$C_{12}$ alkyl.

5. The compound according to claim 1, where $X^1$ is $(CH_2)_m$ and Z is $(CH_2)_n$ and wherein up to 3 carbon atoms of Z and 3 carbon atoms of $X^1$ are optionally and independently mono- or disubstituted by optionally substituted $C_1$-$C_{12}$ alkyl.

6. The compound according to claim 3, wherein at least one alkylene unit of X1 or Z is replaced by —O—, —S—, —SO—, —SO$_2$—, or —NR—.

7. The compound according to claim 5 wherein at least one alkylene unit of X1 and one alkylene unit of Z is replaced by —O—, —S—, —SO—, —SO$_2$—, or —NR—.

8. The compound according to claim 1, having the formula

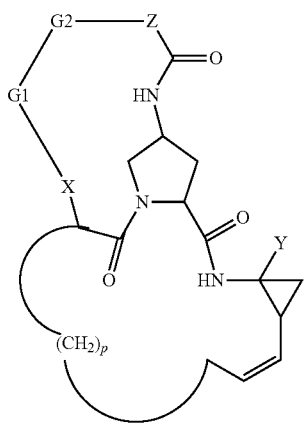

wherein p is 4-7; or wherein p is 4-7, and wherein up to three alkylene units of $(CH_2)_p$ are independently replaced by —O—, —S—, —SO—, —SO$_2$—, or —NR—; or wherein p is 4-7, and wherein up to 3 carbon atoms of A are independently substituted by R1.

9. The compound according to claim 1, having a formula selected from the group consisting of:

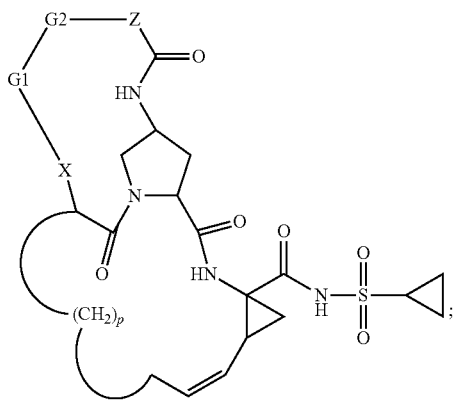

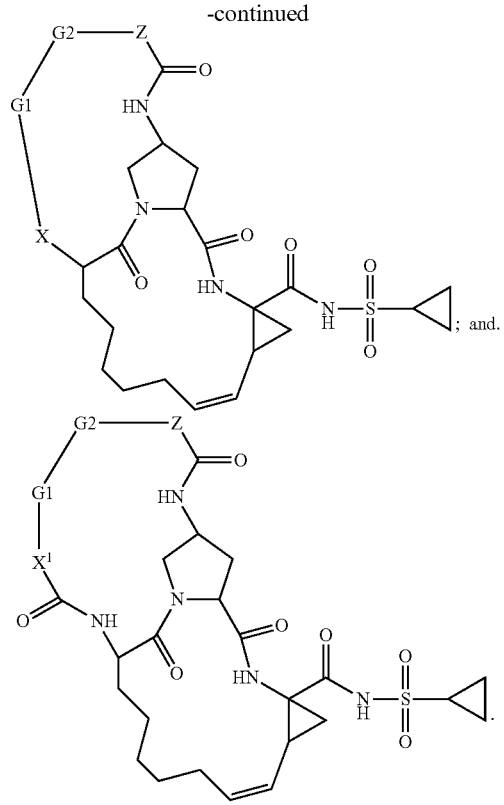

10. The compound according to claim 1, wherein G1 and G2 are each independently selected from the group consisting of

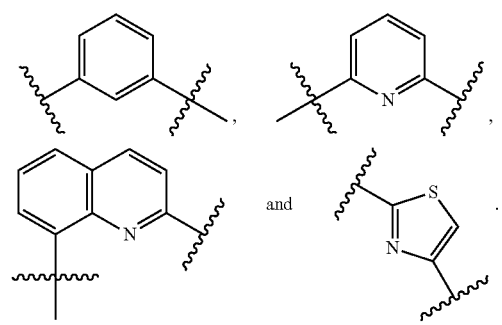

11. A compound according to claim 1 selected from the compounds of Table 1.

12. A method of inhibiting hepatitis C virus comprising administering to a patient a compound according to claim 1.

13. A pharmaceutical composition comprising a therapeutically effective amount of a compound according to claim 1, and a pharmaceutically acceptable diluent, adjuvant or excipient.

14. A pharmaceutical composition according to claim 13, further comprising an additional anti-hepatitis C agent.

15. The composition according to claim 14, wherein said additional anti-hepatitas C agent is selected from the group consisting of interferon, interferon, ribivarin, adamantine, an inhibitor of hepatitis C virus helicase, an inhibitor of hepatitis C virus polymerase, an inhibitor of hepatitis C virus metalloprotease, and an inhibitor of hepatitis C virus IRES.

16. A composition according to claim 13, further comprising a compound that inhibits cytochrome p450.

17. A method of treating hepatitis C infection in a subject comprising administering to a patient a composition according to claim 13.

18. The method according to claim 17, further comprising administering to said subject an additional anti-hepatitis C agent.

19. The method according to claim 18, wherein said additional agent is selected from the group consisting of interferon, interferon, ribivarin, adamantine, an inhibitor of hepatitis C virus helicase, an inhibitor of hepatitis C virus polymerase, an inhibitor of hepatitis C virus metalloprotease, and an inhibitor of hepatitis C virus IRES.

20. A method according to claim 17, further comprising administering to said patient a compound that inhibits cytochrome p450.

\* \* \* \* \*

UNITED STATES PATENT AND TRADEMARK OFFICE
CERTIFICATE OF CORRECTION

PATENT NO. : 8,703,700 B2 Page 1 of 1
APPLICATION NO. : 13/322120
DATED : April 22, 2014
INVENTOR(S) : Majer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 207 days.

Signed and Sealed this

Twenty-ninth Day of September, 2015

Michelle K. Lee
*Director of the United States Patent and Trademark Office*